(12) United States Patent
Gao et al.

(10) Patent No.: US 8,075,852 B2
(45) Date of Patent: Dec. 13, 2011

(54) SYSTEM AND METHOD FOR BUBBLE REMOVAL

(75) Inventors: Chuan Gao, Sunnyvale, CA (US); Tianyue Yu, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 921 days.

(21) Appl. No.: 11/761,007

(22) Filed: Jun. 11, 2007

(65) Prior Publication Data
US 2007/0267335 A1    Nov. 22, 2007

Related U.S. Application Data

(63) Continuation-in-part of application No. 11/760,948, filed on Jun. 11, 2007, and a continuation-in-part of application No. 11/553,944, filed on Oct. 27, 2006, application No. 11/761,007, filed on Jun. 11, 2007, which is a continuation-in-part of application No. 11/760,938, filed on Jun. 11, 2007, and a continuation-in-part of application No. 11/553,944, filed on Oct. 27, 2006.

(60) Provisional application No. 60/813,547, filed on Jun. 13, 2006, provisional application No. 60/814,014, filed on Jun. 14, 2006, provisional application No. 60/814,316, filed on Jun. 15, 2006, provisional application No. 60/814,474, filed on Jun. 16, 2006, provisional application No. 60/815,506, filed on Jun. 20, 2006, provisional application No. 60/816,099, filed on Jun. 22, 2006, provisional application No. 60/942,792, filed on Jun. 8, 2007, provisional application No. 60/732,538, filed on Nov. 2, 2005.

(51) Int. Cl.
*B01L 3/02* (2006.01)

(52) U.S. Cl. ........ 422/502; 422/503; 422/504; 422/505; 422/552; 436/43; 436/180

(58) Field of Classification Search .......... 422/502–505, 422/552; 436/180, 43
See application file for complete search history.

(56) References Cited

U.S. PATENT DOCUMENTS

| | | | |
|---|---|---|---|
| 1,750,245 | A | 3/1930 | Schwedler |
| 3,614,856 | A | 10/1971 | Sanz et al. |
| 3,631,654 | A | 1/1972 | Riely et al. |
| 3,690,836 | A | 9/1972 | Buissiere et al. |
| 3,778,971 | A | 12/1973 | Granger et al. |
| 4,007,010 | A | 2/1977 | Woodbridge, III |
| 4,426,451 | A | 1/1984 | Columbus |
| 4,490,216 | A | 12/1984 | McConnell |
| 4,591,550 | A | 5/1986 | Hafeman et al. |
| 4,676,274 | A | 6/1987 | Brown |
| 4,704,353 | A | 11/1987 | Humphries et al. |
| 4,723,129 | A | 2/1988 | Endo et al. |

(Continued)

FOREIGN PATENT DOCUMENTS

EP    0378968    12/1989

(Continued)

OTHER PUBLICATIONS

U.S. Appl. No. 08/992,025, filed Dec. 1997, Anderson et al.

(Continued)

*Primary Examiner* — Brian R Gordon

(57) ABSTRACT

In one aspect of the invention, systems, methods, and devices are provided for handling liquid. In some embodiments, such systems, methods, and devices are used to combine fluids while removing gaseous bubbles.

15 Claims, 11 Drawing Sheets

U.S. PATENT DOCUMENTS

| | | | |
|---|---|---|---|
| 4,758,786 A | 7/1988 | Hafeman | |
| 4,789,628 A | 12/1988 | Nayak | |
| 4,790,640 A | 12/1988 | Nason | |
| 4,792,283 A | 12/1988 | Okayasu | |
| 4,849,330 A | 7/1989 | Humphries et al. | |
| 4,849,340 A | 7/1989 | Oberhardt | |
| 4,858,883 A | 8/1989 | Webster | |
| 4,883,579 A | 11/1989 | Humphries et al. | |
| 4,911,794 A | 3/1990 | Parce et al. | |
| 4,915,812 A | 4/1990 | Parce | |
| 4,946,795 A | 8/1990 | Gibbons et al. | |
| 4,963,815 A | 10/1990 | Hafeman | |
| 5,053,060 A | 10/1991 | Kopf-Sill et al. | |
| 5,104,792 A | 4/1992 | Silver et al. | |
| 5,126,022 A | 6/1992 | Soane et al. | |
| 5,127,730 A | 7/1992 | Brelje et al. | |
| 5,143,854 A | 9/1992 | Pirrung et al. | |
| 5,164,319 A | 11/1992 | Hafeman et al. | |
| 5,171,132 A | 12/1992 | Miyazaki et al. | |
| 5,188,963 A | 2/1993 | Stapleton | |
| 5,200,152 A * | 4/1993 | Brown | 422/503 |
| 5,200,313 A | 4/1993 | Carrico | |
| 5,215,131 A | 6/1993 | Poy | |
| 5,219,712 A | 6/1993 | Evans et al. | |
| 5,221,326 A | 6/1993 | Yamaguchi et al. | |
| 5,229,297 A | 7/1993 | Schnipelsky et al. | |
| 5,230,866 A | 7/1993 | Shartle et al. | |
| 5,252,294 A | 10/1993 | Kroy et al. | |
| 5,271,724 A | 12/1993 | van Lintel | |
| 5,275,787 A | 1/1994 | Yuguchi et al. | |
| 5,277,556 A | 1/1994 | van Lintel | |
| 5,281,516 A | 1/1994 | Stapleton et al. | |
| 5,296,375 A | 3/1994 | Kricka et al. | |
| 5,304,487 A | 4/1994 | Wilding et al. | |
| 5,313,264 A | 5/1994 | Ivarsson et al. | |
| 5,346,672 A | 9/1994 | Stapleton et al. | |
| 5,375,979 A | 12/1994 | Trah | |
| 5,382,511 A | 1/1995 | Stapleton | |
| 5,384,261 A | 1/1995 | Winkler et al. | |
| 5,395,503 A | 3/1995 | Parce et al. | |
| 5,424,186 A | 6/1995 | Fodor et al. | |
| 5,436,129 A | 7/1995 | Stapleton | |
| 5,443,985 A | 8/1995 | Lu et al. | |
| 5,451,500 A | 9/1995 | Stapleton | |
| 5,486,335 A | 1/1996 | Wilding et al. | |
| 5,498,392 A | 3/1996 | Wilding et al. | |
| 5,500,188 A | 3/1996 | Hafeman et al. | |
| 5,580,523 A | 12/1996 | Bard | |
| 5,585,069 A | 12/1996 | Zanzucchi | |
| 5,587,128 A | 12/1996 | Wilding et al. | |
| 5,589,350 A | 12/1996 | Bochner | |
| 5,593,130 A | 1/1997 | Hansson et al. | |
| 5,605,653 A | 2/1997 | DeVos et al. | |
| 5,610,010 A | 3/1997 | Surzycki et al. | |
| 5,631,134 A | 5/1997 | Cantor | |
| 5,639,423 A | 6/1997 | Northrup et al. | |
| 5,646,039 A | 7/1997 | Northrup et al. | |
| 5,653,939 A | 8/1997 | Hollis et al. | |
| 5,660,993 A | 8/1997 | Cathey et al. | |
| 5,677,195 A | 10/1997 | Winkler et al. | |
| 5,699,462 A | 12/1997 | Fouquet et al. | |
| 5,700,637 A | 12/1997 | Southern | |
| 5,726,026 A | 3/1998 | Wilding et al. | |
| 5,843,767 A | 12/1998 | Beattie | |
| 5,856,174 A | 1/1999 | Lipshutz et al. | |
| 5,858,195 A | 1/1999 | Ramsey | |
| 5,863,801 A | 1/1999 | Southgate | |
| 5,866,434 A | 2/1999 | Massey et al. | |
| 5,871,928 A | 2/1999 | Fodor et al. | |
| 5,876,918 A | 3/1999 | Wainwright et al. | |
| 5,882,903 A | 3/1999 | Andrevski et al. | |
| 5,922,591 A | 7/1999 | Anderson et al. | |
| 5,945,334 A | 8/1999 | Besemer et al. | |
| 5,952,173 A | 9/1999 | Hansmann | |
| 5,976,336 A | 11/1999 | Dubrow et al. | |
| 5,980,742 A | 11/1999 | Saitoh | |
| 6,001,229 A | 12/1999 | Ramsey | |
| 6,001,231 A | 12/1999 | Kopf-Sill | |
| 6,010,607 A | 1/2000 | Ramsey | |
| 6,010,608 A | 1/2000 | Ramsey | |
| 6,033,546 A | 3/2000 | Ramsey | |
| 6,040,138 A | 3/2000 | Lockhart et al. | |
| 6,043,080 A | 3/2000 | Anderson et al. | |
| 6,065,864 A | 5/2000 | Evans et al. | |
| 6,071,081 A | 6/2000 | Shiraishi | |
| 6,077,674 A | 6/2000 | Schleifer et al. | |
| 6,090,553 A | 7/2000 | Matson | |
| 6,117,396 A * | 9/2000 | Demers | 422/504 |
| 6,130,098 A | 10/2000 | Handique et al. | |
| 6,140,044 A | 10/2000 | Besemer et al. | |
| 6,143,496 A | 11/2000 | Brown et al. | |
| 6,168,948 B1 | 1/2001 | Anderson et al. | |
| 6,186,659 B1 | 2/2001 | Schembri | |
| 6,197,595 B1 | 3/2001 | Anderson et al. | |
| 6,258,593 B1 | 7/2001 | Schembri | |
| 6,271,145 B1 | 8/2001 | Toda | |
| 6,287,850 B1 | 9/2001 | Besemer et al. | |
| 6,326,211 B1 * | 12/2001 | Anderson et al. | 436/177 |
| 6,399,365 B2 | 6/2002 | Besemer et al. | |
| 6,420,114 B1 | 7/2002 | Bedilion | |
| 6,513,968 B2 | 2/2003 | Schembri | |
| 6,551,817 B2 | 4/2003 | Besemer et al. | |
| 6,613,513 B1 | 9/2003 | Parce et al. | |
| 6,613,529 B2 | 9/2003 | Bedilion | |
| 6,648,853 B1 | 11/2003 | McEntee | |
| 6,682,702 B2 | 1/2004 | Barth | |
| 6,716,629 B2 | 4/2004 | Hess et al. | |
| 6,733,977 B2 | 5/2004 | Besemer et al. | |
| 6,811,752 B2 * | 11/2004 | Barbera-Guillem | 422/503 |
| 6,830,936 B2 | 12/2004 | Anderson et al. | |
| 6,875,619 B2 | 4/2005 | Blackburn | |
| 6,905,816 B2 | 6/2005 | Jacobs et al. | |
| 6,911,183 B1 * | 6/2005 | Handique et al. | 422/502 |
| 7,018,842 B2 | 3/2006 | Dorsel | |
| 7,025,935 B2 * | 4/2006 | Jones et al. | 422/503 |
| 7,033,761 B2 | 4/2006 | Shafer | |
| 7,125,523 B2 | 10/2006 | Sillman | |
| 7,129,554 B2 | 10/2006 | Lieber et al. | |
| 7,318,912 B2 * | 1/2008 | Pezzuto et al. | 422/504 |
| 7,332,127 B2 | 2/2008 | Kim et al. | |
| 7,351,377 B2 * | 4/2008 | Chazan et al. | 422/502 |
| 7,351,379 B2 | 4/2008 | Schleifer | |
| 7,364,895 B2 | 4/2008 | Besemer et al. | |
| 7,371,348 B2 | 5/2008 | Schleifer | |
| 7,390,457 B2 | 6/2008 | Schembri | |
| 7,476,360 B2 | 1/2009 | Gau et al. | |
| 7,641,871 B2 | 1/2010 | Futami et al. | |
| 7,674,616 B2 * | 3/2010 | Farnam et al. | 435/287.1 |
| 7,842,234 B2 * | 11/2010 | Lauks et al. | 422/50 |
| 2002/0022261 A1 | 2/2002 | Anderson et al. | |
| 2002/0055167 A1 | 5/2002 | Pourahmadi et al. | |
| 2003/0148362 A1 | 8/2003 | Luka | |
| 2003/0231985 A1 | 12/2003 | Schleifer | |
| 2003/0232379 A1 | 12/2003 | Amorese | |
| 2003/0235520 A1 | 12/2003 | Shea | |
| 2004/0086424 A1 * | 5/2004 | Schembri | 422/58 |
| 2004/0086868 A1 | 5/2004 | Parker | |
| 2004/0106130 A1 | 6/2004 | Besemer et al. | |
| 2004/0166525 A1 | 8/2004 | Besemer et al. | |
| 2004/0171054 A1 | 9/2004 | Besemer et al. | |
| 2004/0214310 A1 | 10/2004 | Parker | |
| 2005/0003421 A1 | 1/2005 | Besemer et al. | |
| 2005/0026299 A1 | 2/2005 | Bhattacharjee | |
| 2005/0084895 A1 | 4/2005 | Besemer et al. | |
| 2005/0089953 A1 | 4/2005 | Besemer et al. | |
| 2005/0100946 A1 | 5/2005 | Lipshutz et al. | |
| 2005/0106615 A1 | 5/2005 | Besemer et al. | |
| 2005/0106617 A1 | 5/2005 | Besemer et al. | |
| 2005/0106618 A1 | 5/2005 | Besemer et al. | |
| 2005/0158819 A1 | 7/2005 | Besemer et al. | |
| 2005/0202504 A1 | 9/2005 | Anderson et al. | |
| 2005/0208646 A1 | 9/2005 | Besemer et al. | |
| 2005/0250199 A1 | 11/2005 | Anderson et al. | |
| 2006/0040380 A1 | 2/2006 | Besemer et al. | |
| 2006/0234267 A1 | 10/2006 | Besemer et al. | |
| 2006/0246490 A1 | 11/2006 | Anderson et al. | |
| 2007/0099288 A1 | 5/2007 | Gao et al. | |

| | | | |
|---|---|---|---|
| 2007/0267782 | A1 | 11/2007 | Gao et al. |
| 2008/0038713 | A1 | 2/2008 | Gao et al. |
| 2008/0038714 | A1 | 2/2008 | Gao et al. |
| 2008/0311585 | A1 | 12/2008 | Gao et al. |
| 2009/0143249 | A1 | 6/2009 | Besemer et al. |
| 2010/0196212 | A1* | 8/2010 | Reed et al. .................... 422/100 |
| 2010/0261286 | A1* | 10/2010 | Kim et al. .................... 436/149 |

FOREIGN PATENT DOCUMENTS

| | | |
|---|---|---|
| WO | WO 90/04645 | 5/1990 |
| WO | WO 90/15070 | 12/1990 |
| WO | WO 92/10092 | 6/1992 |
| WO | WO 92/10587 | 6/1992 |
| WO | WO 92/10588 | 6/1992 |
| WO | WO 93/09668 | 5/1993 |
| WO | WO 93/22053 | 11/1993 |
| WO | WO 93/22058 | 11/1993 |
| WO | WO 94/03791 | 2/1994 |
| WO | WO 94/05414 | 3/1994 |
| WO | WO 98/52691 | 11/1998 |

OTHER PUBLICATIONS

U.S. Appl. No. 09/519,148, filed Mar. 2000, Lipshutz et al.
U.S. Appl. No. 12/842,977, filed Jul. 2010, Besemer et al.
Anderson et al., "Microfluidic biochemical analysis system," Technical Digest of Transducers '97, International Conference on Solid-State Sensors and Actuators, Chicago, pp. 477-480 (1977).
Anderson et al., "Microfluidic Genetic Analysis Systems: Improvements and Methods," Abstract for 1998 Solid-State Sensor and Actuator Workshop, 4 pages, Jun. 7-11, 1998.
Anderson et al., "Miniaturized genetic-analysis system," Technical Digest of 1996 Solid-State Sensor and Actuator Workshop, Hilton Head Island, South Carolina, pp. 258-261 (1996).
Andersson et al., "Biological Cell Assays on an Electrokinetic Microchip," Technical Digest of Transducers '97, International Conference on Solid-State Sensors and Actuators, Chicago, pp. 1311-1314 (1997).
Bart et al., "Microfabricated Electrophydrodynamic Pumps," Sensors and Actuators, A21-A23:193-197 (1990).
Bousse et al., "Biosensor for Detection of Enzymes Immbolized in Microvolume Reaction Chambers," Sensors and Actuators, vol. B1, pp. 555-560 (1990).
Dynal Inc., Biomagnetic Techniques in Molecular Biology, A Technical Handbook 3rd Edition pp. 7-10, 48-50, (1998).
Effenhauser et al., "Glass Chips for High-Speed Capillary Electrophoresis Separations with Submicrometer Plate Heights," Anal. Chem., 65:2637-2642 (1993).
Effenhauser et al., "High-Speed Separation of Antisense Oligonucleotides on a Micromachined Capillary Electrophoresis Device," Anal. Chem., 66:2949-2953 (1994).
Fodor et al., "Light-Directed, Spatially Addressable Parallel Chemical Synthesis," Science, 251:767-773 (1991).
Ghandi, VLSI Fabrication Principles, 2nd ed., John Wiley & Sons, Inc., Ch. 10 (1994).
Harrison and Chiem, "Immunoassay flow systems on-chip," Technical Digest of 1996 Solid-State Sensor and Actuator Workshop, Hilton Head Island, South Carolina, pp. 5-8 (1996).
Harrison et al., "Micromachining a Miniaturized Capillary Electrophoresis-Based Chemical Analysis System on a Chip," Science, 261:895-897 (1993).
Hein et al., "Bubble Motion Induced by Marangoni Convection Under the Influence of Gravity," Chem. Eng. Technol. (1998) 21:41-44.

Horowitz and Hill, The Art of Electronics, 2d ed., Cambridge University Press, Ch. 15 (1994).
Jacobsen et al., "High-Speed Separations on a Microchip," Anal. Chem., 66:1114-1118 (1994).
Kenis et al., "Fabrication inside Microchannels Using Fluid Flow," Accounts of Chemical Research, 33, pp. 841-847 (2000).
Kenis et al., "Microfabrication Inside Capillaries Using Multiphase Laminar Flow Patterning," Science, 285, 83-85 (1999).
Li et al., "Transport, manipulation, and reaction of biological cells on-chip using electrokinetic effects," Anal. Chem., vol. 69, No. 8, pp. 1564-1568 (1997).
Luckey et al., "A model for the mobility of single-stranded DNA in capillary gel electrophoresis," Electrophoresis, 14:492-501 (1993).
Man et al., "Microfluidic Plastic Capillaries on Silicon Substrates: A New Inexpensive Technology for Bioanalysis Chips," Proceedings IEEE Tenth Annual International Workshop on Mechanical Systems, Nagoya, Japan, pp. 311-316 (Jan. 26-30, 1997).
Manz et al., "Planar chips technology for miniaturization and integration of separation techniques into monitoring systems: Capillary electrophoresis on a chip," J. Chromatog., 593:253-258 (1992).
Nyborg, "Acoustical streaming," Physical Acoustics, Principles and Methods, vol. 2., Part B, Mason, ed., Academic Press (1965), Chapter 11, pp. 265-333.
Oosterbroek, Preface in Lab-on-a-Chip: miniaturized systems for (bio) chemical analysis and synthesis, Elsevier, pp. v-vi (2003).
Owicki et al., "The Light-Addressable Potentiometric Sensor: Principles and Biological Applications," Annu. Rev. Biophys. Biomol. Struct., vol. 23, pp. 87-113 (1994).
Patent Interference No. 105,285, United States Patent and Trademark Office, *Schembri*, Patent 6,513,968 v. *Besemer*, U.S. Appl. No. 10/619,224 (Jul. 2006).
Patent Interference No. 105,440, United States Patent and Trademark Office, *Bedilion*, Patent No. 6,420,114 and 6,613,529 v. *Besemer*, U.S. Appl. No. 10/639,696 (Aug. 2006).
Pease et al., "Light-generated oligonucleotide arrays for rapid DNA sequence analysis," PNAS, 91:5022-5026 (1994).
Piezoelectric Technology, Data for Engineers, Clevite Corp.
Richter et al., "A micromachined electrohydrodynamic (EHD) pump," Sensors and Actuators, 29:159-165 (1991).
Richter et al., "An Electrohydrodynamic Micropump," 3rd IEEE Workshop on Micro Electro Mechanical Systems, Feb. 12-14, 1990, Napa Valley.
Staecker et al., "A Procedure for RT-PCR Amplification of mRNAs on Histological Specimens," BioTechniques, vol. 16, No. 1, pp. 76-80 (Jan. 1994).
Stix, "Gene Readers," Scientific American, pp. 149-150 (Jan. 1994).
Woolley and Mathies, "Ultra high-speed DNA fragment separations using microfabricated capillary array electrophoresis chips," PNAS, 91:11348-11352 (1994).
Woolley et al., "Functional integration of PCR amplification and capillary electrophoresis in a microfabricated DNA analysis device," Anal. Chem., vol. 68, No. 23, pp. 4081-4086 (1996).
Matsuoka et al., "Phase separation of organic-aqueous droplet and segmented mixed phase flows by using a capillary restricted surface modification," $9^{th}$ International Conference on Miniaturized Systems for Chemistry and Life Sciences, Oct. 9-13, 2005, Boston, Massachusetts, pp. 1143-1145 (2005).
Clevite Corporation, Piezoelectric Division, "Piezoelectric technology data for engineers," Bedford, OH (1965).

* cited by examiner

| | 200 micron depth |
| | 400 micron depth |
| | 20 micron depth |

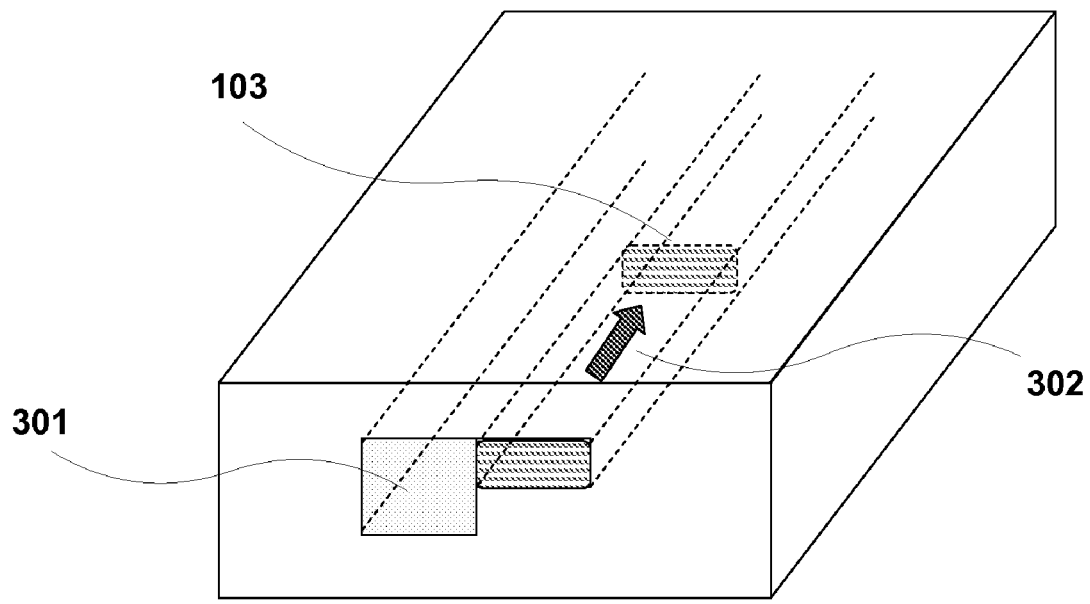
FIG. 3a
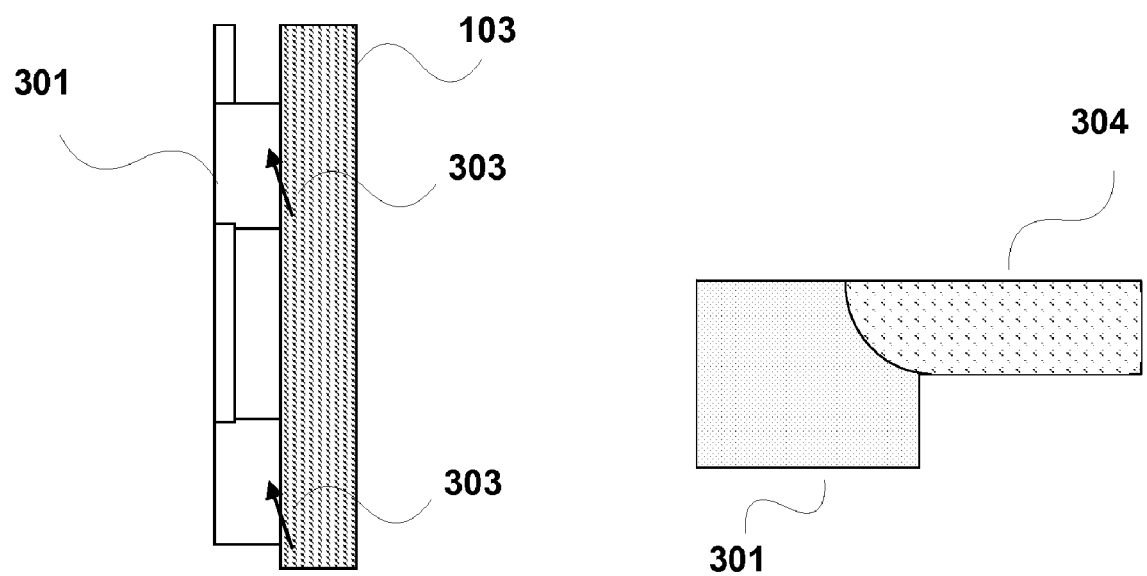
FIG. 3b
FIG. 3c

SYSTEM AND METHOD FOR BUBBLE REMOVAL

RELATED APPLICATIONS

The present application is a continuation in part of U.S. patent application Ser. No. 11/760,948, filed Jun. 11, 2007 and a continuation in part of U.S. patent application Ser. No. 11/760,938, filed Jun. 11, 2007, which both claim priority from U.S. Provisional Patent Application Ser. No. 60/813,547, filed Jun. 13, 2006, and claim priority from U.S. Provisional Patent Application Ser. No. 60/814,014, filed Jun. 14, 2006, and claim priority from U.S. Provisional Patent Application Ser. No. 60/814,316, filed Jun. 15, 2006, and claim priority from U.S. Provisional Patent Application Ser. No. 60/814,474, filed Jun. 16, 2006, and claim priority from U.S. Provisional Patent Application Ser. No. 60/815,506, filed Jun. 20, 2006, and claim priority from U.S. Provisional Patent Application Ser. No. 60/816,099, filed Jun. 22, 2006, and claim priority from U.S. Provisional Patent Application Ser. No. 60/942,792, filed Jun. 11, 2007, and are continuation in part of U.S. patent application Ser. No. 11/553,944, filed Oct. 27, 2006. Each application is hereby incorporated by reference herein in its entirety for all purposes.

BACKGROUND OF THE INVENTION

This application relates to methods, devices, systems for fluid handling. The field of nucleic acid assays has been transformed by microarrays which allow extremely high-throughput and parallel monitoring of gene expression events, expression profiling, diagnostics and large-scale, high-resolution analyses, among other applications. Microarrays are used in biological research, clinical diagnostics, drug discovery, environmental monitoring, forensics and many other fields.

Current genetic research generally relies on a multiplicity of distinct processes to elucidate the nucleic acid sequences, with each process to introducing a potential for error into the overall process. These processes also draw from a large number of distinct disciplines, including chemistry, molecular biology, medicine and others. It would therefore be desirable to integrate the various process used in genetic diagnosis, in a single process, at a minimum cost, and with a maximum ease of operation.

Interest has been growing in the fabrication of microfluidic devices. Typically, advances in the semiconductor manufacturing arts have been translated to the fabrication of micromechanical structures, e.g., micropumps, microvalves and the like, and microfluidic devices including miniature chambers and flow passages.

A number of researchers have attempted to employ these microfabrication techniques in the miniaturization of some of the processes involved in genetic analysis in particular. Conventional approaches often will inevitably involve extremely complicated fluidic networks as more and more reagents are added into systems, and more samples are processed. By going to a smaller platform, such fluidic complexity brings many concerns such as difficulty in fabrication, higher manufacture cost, lower system reliability, etc. Thus, there's a need to have a simpler way to process samples and perform the reactions in a controlled fashion. However, there remains a need for an apparatus which simplifies and combines the processing of multiple samples and performing the multiple reactions and steps involved in the various operations in the nucleic acid analysis. During the processing of samples, it is often desirable to provide an efficient and effective way to mix the fluids. Various embodiments of the present invention meet one or more of these and other needs.

BRIEF SUMMARY OF THE INVENTION

An embodiment of the present invention provides systems and methods for bubble removal for lab cards, such as microfluidic lab cards. In one aspect of the present invention, systems, methods, and computer software products are provided for bubble removal and sample preparation of biological assays. Merely by way of example, the invention is described as it applies to preparing nucleic acid samples for hybridization with microarrays, but it should be recognized that the invention has a broader range of applicability.

According to an embodiment of the present invention, an apparatus, method and a system for removing a bubble are provided which includes a first substrate having an inner surface that defines a top surface of at least one chamber, a second substrate having inner surfaces that define the chamber and at least one venting channel there between the first substrate and the second substrate, and a third substrate having inner surfaces that define at least one main channel leading into a bottom entrance of the chamber connected to a bottom surface of the chamber in the second substrate. The bottom surface of the chamber is coated to provide a hydrophobic surface. In addition, the bottom surface of the chamber is adapted with a radius to retain a quantity of a first fluid and a second fluid such that the surface tension of the bottom surface maintains the fluids in contact with the bottom surface of the chamber. A pressurized gas is used for moving the fluids. As the fluids are collected into the chamber, the bubble between the first fluid and the second fluid is dispelled in the chamber resulting in the removal of the bubble from the fluids.

According to another embodiment of the present invention, the chamber includes a radius such that the surface tension of the bottom surface of the chamber maintains the fluid in contact with the bottom surface of the chamber. In a preferred embodiment of the present invention, the chamber is adapted with a first radius to retain a quantity of fluid. The first radius of the bottom surface of the chamber is in the range of 1 to 20 mm, preferably in the range of 2 to 10 mm, and most preferred in the range of 2 to 4 mm. According to another preferred embodiment of the present invention, the apparatus described above is provided with a second radius to further assure the retention of the fluids at the bottom of the chamber while the bubble is being removed. In a preferred embodiment, the second radius is in the range of 1 mm to 20 mm, more preferably 2 mm to 4 mm and most preferably 1 mm to 2 mm.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 2 illustrates the various depths of the sections of the system of channels in FIG. 1 according to an embodiment of the present invention. FIG. 2b illustrates another embodiment of the channel design which is indicated as "110" in FIG. 1.

FIG. 2c illustrates another embodiment of the channel design which is indicated as "111" in FIG. 1. FIG. 2d illustrates another embodiment of the channel design which is indicated as "112" in FIG. 1. FIG. 2e illustrates another embodiment of the channel design which is indicated as "113" in FIG. 1.

FIG. 3 illustrates an alternative embodiment of the bubble removing mechanism design which describes various physical shapes and configuration of the channels. FIG. 3a illustrates the channel design where the bubble removing mechanism is rectangular in shape and located at the side of the main channel. FIG. 3b illustrates a side view of the bubble removing mechanism and the main channel. FIG. 3c illustrates the appearance of the shape of the fluid in the channel.

FIG. 4 illustrates an alternative embodiment of the bubble removing mechanism design which describes various physical shapes and configuration of the channels.

FIG. 6 illustrates further details of the first substrate of the system illustrated in FIG. 5 according to an embodiment of the present invention.

FIG. 7 illustrates further details of the second substrate of the system illustrated in FIG. 5 according to an embodiment of the present invention.

FIG. 9 illustrates an alternative embodiment of steps for removing a bubble while collecting the fluids in a chamber.

FIG. 10 illustrates an alternative embodiment of a mixing method of multiple reagents.

DETAILED DESCRIPTION OF THE INVENTION

I. General Description

Figures 1, 2A:
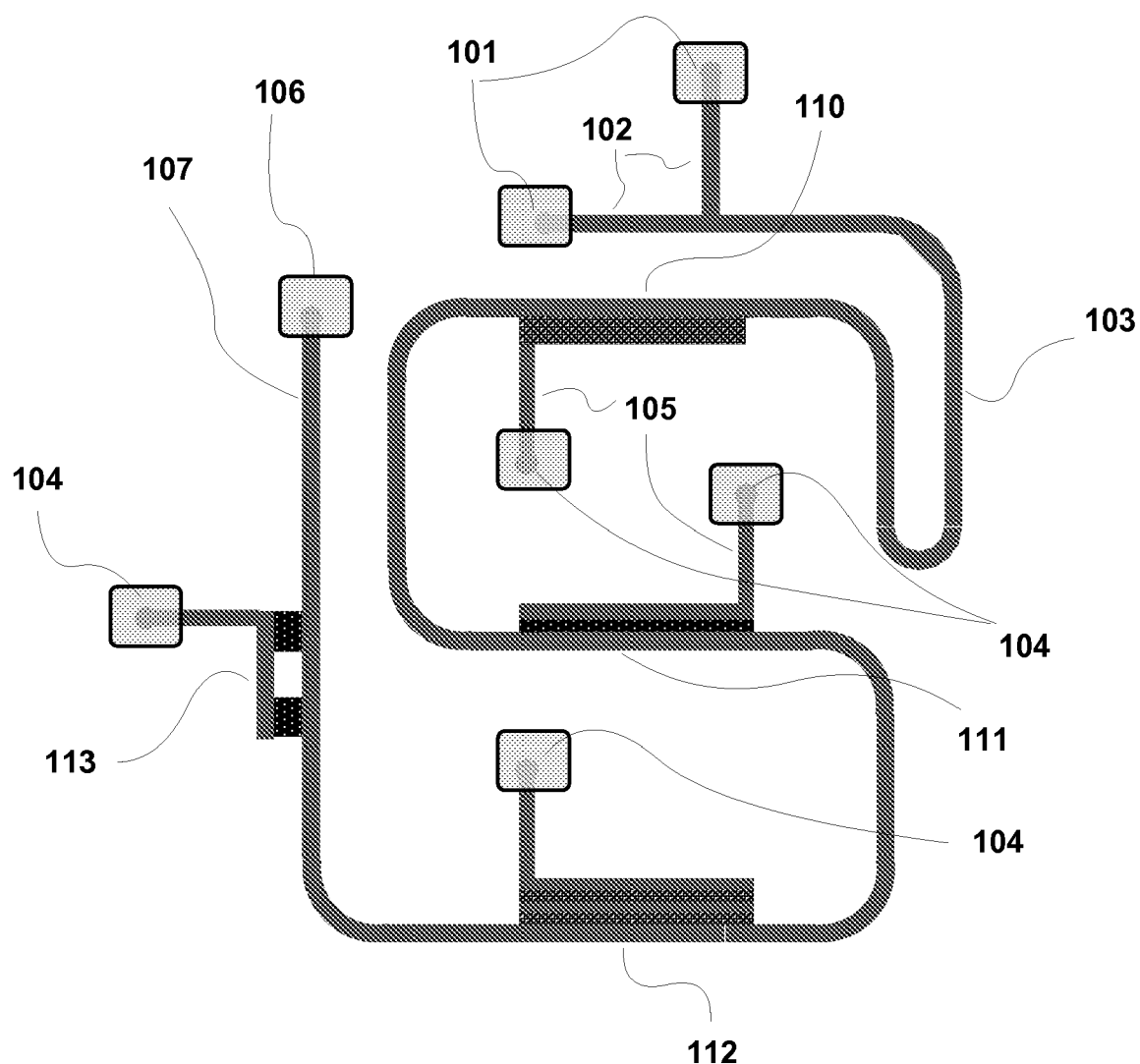
FIG. 1 is an image of a system for introducing multiple reagents and adding them sequentially according to an embodiment of the present invention.
FIG. 2a illustrates an embodiment of the channel design which indicates a preferred embodiment of various depths.

The present invention cites certain patents, applications and other references. When a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285 (International Publication Number WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098.

Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip R. Example arrays are shown on the website at affymetrix.com.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 15 10/442,021, 10/013,598 (U.S. patent application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871, 928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g. *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965, 188, and 5,333,675, and each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in U.S. Pat. Nos. 5,242, 794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491 (U.S. patent application Publication 20030096235), 09/910,292 (U.S. patent application Publication 20030082543), and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2nd Ed. Cold Spring Harbor, N.Y., 1989); Berger and Kimmel *Methods in Enzymology*, Vol. 152, Guide to Molecular Cloning Techniques (Academic Press, Inc., San Diego, Calif., 1987); Young and Davism, *P.N.A.S.* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biolog Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/197,621, 10/063,559 (United States Publication No. 20020183936), 10/065,856, 10/065,868, 10/328, 818, 10/328,872, 10/423,403, and 60/482,389.

II. Definitions

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Biopolymer or biological polymer: is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. "Biopolymer synthesis" is intended to encompass the synthetic production, both organic and inorganic, of a biopolymer.

Related to a bioploymer is a "biomonomer" which is intended to mean a single unit of biopolymer, or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, etc., for example, are also biomonomers. initiation Biomonomer: or "initiator biomonomer" is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

Complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa *Nucleic Acids Res.* 12:203 (1984), incorporated herein by reference.

Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

Effective amount refers to an amount sufficient to induce a desired result.

Genome is all the genetic material in the chromosomes of an organism. DNA derived from the genetic material in the chromosomes of a particular organism is genomic DNA.

A genomic library is a collection of clones made from a set of randomly generated overlapping DNA fragments representing the entire genome of an organism. Hybridization conditions will typically include salt concentrations of less than about 1 M, more usually less than about 500 mM and preferably less than about 200 mM. Hybridization temperatures can be as low as 5.degree. C., but are typically greater than 22.degree. C., more typically greater than about 30.degree. C., and preferably in excess of about 37.degree. C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Hybridizations, e.g., allele-specific probe hybridizations, are generally performed under stringent conditions. For example, conditions where the salt concentration is no more than about 1 Molar (M) and a temperature of at least 25 degrees Celsius (° C.), e.g., 750 mM NaCl, 50 mM NaPhosphate, 5 mM EDTA, pH 7.4 (5×SSPE) and a temperature of from Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "*Molecular Cloning A laboratory Manual*" 2nd Ed. Cold Spring Harbor Press (1989) which is hereby incorporated by reference in its entirety for all purposes above.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridization probes are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics.

Hybridizing specifically to: refers to the binding, duplexing, or hybridizing of a molecule only to a particular nucleotide sequence or sequences under stringent conditions when that sequence is present in a complex mixture (e.g., total cellular) DNA or RNA.

Isolated nucleic acid is an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

Ligand: A ligand is a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies. Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

Mixed population or complex population: refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

Monomer: refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer.

The term "monomer" also refers to a chemical subunit that can be combined with a different chemical subunit to form a compound larger than either subunit alone. mRNA or mRNA transcripts: as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Nucleic acid library or array is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

Probe: A probe is a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Primer is a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

Target: A molecule that has an affinity for a given probe. Targets may be naturally occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

WGSA (Whole Genome Sampling Assay) Genotyping Technology: A technology that allows the genotyping of hundreds of thousands of SNPS simultaneously in complex DNA without the use of locus-specific primers. In this technique, genomic DNA, for example, is digested with a restriction enzyme of interest and adaptors are ligated to the digested fragments. A single primer corresponding to the adaptor sequence is used to amplify fragments of a desired size, for example, 500-2000 bp. The processed target is then hybridized to nucleic acid arrays comprising SNP-containing fragments/probes. WGSA is disclosed in, for example, U.S. Provisional Application Ser. Nos. 60/319,685; 60/453,930, 60/454,090 and 60/456,206, 60/470,475, U.S. patent applications Ser. Nos. 09/766,212, 10/316,517, 10/316,629, 10/463,991, 10/321,741, 10/442,021 and 10/264,945, each of which is hereby incorporated by reference in its entirety for all purposes.

Whole Transcript Assay (WTA) is used herein: a WTA is an assay protocol that can representatively sample entire transcripts (i.e., all exons in a transcript).

III. Specific Embodiments

Some embodiments of the present invention provide systems and methods for bubble removal for microfluidic devices, such as lab cards. In one aspect of the present invention, systems, methods, and computer software products are provided for bubble removal and sample preparation of biological assays. Merely by way of example, the invention is described as it applies to preparing nucleic acid samples using a lab card, but it should be recognized that the invention has a broader range of applicability. In another example, the bubble removing mechanisms are suitable for performing complex chemical and/or biochemical reactions.

In a preferred embodiment of the present invention, the apparatus, method and system of the present invention is directed towards combining fluids while removing gaseous bubbles. Typically, the bubble removing mechanism is utilized in microfluidic systems such as, for example, lab cards or the microfluidic devices described in U.S. Pat. No. 6,168,948 which is incorporated herein in its entirety. In general, a lab card is a disposable part, for example, where reagents are controlled and processed. A microfluidic device generally incorporates a lab card with all the necessary instruments (for example, reusable components) required to control the fluidics and reaction conditions (for example, pressure regulator, valves, computers, mechanical hardware, heaters, coolers, etc).

The body of the lab card, in general, defines the various reaction chambers and fluid passages in which the above described operations are carried out and also includes defining the design and location of the bubble removing mechanism(s). Fabrication of the body, and thus the various chambers, channels, including the bubble removing mechanism(s) disposed within the body may generally be carried out using one or a combination of a variety of well known manufacturing techniques and materials. Generally, the material from which the body is fabricated will be selected so as to provide maximum resistance to the full range of conditions to which the device will be exposed, e.g., extremes of temperature, salt, pH, application of electric fields and the like, and will also be selected for compatibility with other materials used in the device. Additional components may be later introduced, as necessary, into the body. Alternatively, the device may be formed from a plurality of distinct parts that are later assembled or mated. For example, separate bubble removing mechanisms and mixing channels may be assembled to provide additional functions of the device.

As a miniaturized device, the body of the device, for example a lab card, will typically be in the range of 1 to 20 cm in length by in the range of 1 to 15 cm in width by in the range 0.1 to 2.5 cm thick, preferably in the range of 2 to 15 cm in length by in the range of 2 to 10 cm in width by in the range 0.1 to 1.5 cm thick, most preferably about 7.6 cm in length by about 5.1 cm in width by about 0.64 cm. Although indicative of a rectangular shape, it will be readily appreciated that the devices of the present invention may be embodied in any number of shapes depending upon the particular need. Additionally, these dimensions will typically vary depending upon the number of operations to be performed by the device, the complexity of these operations and the like. As a result, these dimensions are provided as a general indication of the size of the device. The number, shape and size of the channels included within the device will also vary depending upon the specific application for which the device is to be used. The number and size of the bubble removing mechanisms included within the device will also vary depending upon the specific application for which the device is to be used. Generally, the device will include at least one bubble removing mechanism and preferably at least one mixing chamber, all integrated within a single body. Individual bubble removing mechanisms will also vary in size and shape according to the specific function of the reaction chamber. For example, in some cases, elongated bubble removing mechanisms may be employed. Alternatively, circular bubble removing mechanisms may be used. In general however, the elongated bubble removing mechanisms will typically range from about 10 to about 10,000 µm in length, from about 10 to about 1,000 µm in width, about 10 to about 1,000 µm deep, preferably 100 to 7,000 µm in length, about 10 to 700 µm width, and about 30 to 1,000 µm deep, most preferably 100 to 5,000 µm in length, about 10 to 500 µm width, and about 50 to 1,000 µm deep.

Circular bubble removing mechanisms, will typically be from about 50 to about 4,000 µm in width or diameter, and about 50 to about 5,000 µm deep, preferably from about 50 to about 3,000 µm in width or diameter and preferably 50 to about 2,000 µm deep, most preferably from about 50 to about 2,000 µm in width or diameter and 50 to about 1,000 µm deep. Mixing channels, on the other hand, are typically distinguished from chambers in having smaller dimensions relative to the bubble removing mechanisms. Although described in terms of bubble removing mechanisms, it will be appreciated that these mechanisms may perform a number of varied functions, e.g., as storage chambers, incubation chambers, mixing chambers and the like.

According to one aspect of the present invention, the surface tension of a channel or chamber in contact with the fluid maintains the fluid in the desired location without having the fluid go into other undesired areas while the gaseous bubble(s) is dispelled in the exposed open areas as described by the following equation:

$$\text{Force} = 2\pi r \sigma_{LG} \cos \theta$$

Where:
R=radius of the crack opening.
$\sigma_{LG}$=liquid-gas surface tension
$\theta$=contact angle In general, the bubble removing mechanism is part of the lab card, therefore, it is usually fabricated as part of the body of the microfluidic device. Although primarily described in terms of producing a fully integrated body of the device, the above described methods can also be used to fabricate individual discrete components of the device which are later assembled into the body of the device. The body of the lab card is generally fabricated using one or more of a variety of methods and materials suitable for microfabrication techniques. For example, in preferred aspects, the body of the device may comprise a number of planar members that may individually be injection molded parts fabricated from a variety of polymeric materials, or may be silicon, glass, or the like. In the case of substrates like silica, glass or silicon, methods for etching, milling, drilling, etc., may be used to produce wells and depressions which make up the various reaction chambers and fluid channels within the device. Microfabrication techniques, such as those regularly used in the semiconductor and microelectronics industries are particularly suited to these materials and methods. These techniques include, e.g., electrodeposition, low-pressure vapor deposition, photolithography, wet chemical etching, reactive ion etching (RIE), laser drilling, and the like. Where these methods are used, it will generally be desirable to fabricate the planar members of the device from materials similar to those used in the semiconductor industry, i.e., silica, silicon, gallium arsenide, polyimide substrates. U.S. Pat. No. 5,252, 294, to Kroy, et al., incorporated herein by reference in its entirety for all purposes, reports the fabrication of a silicon based multiwell apparatus for sample handling in biotechnology applications.

Photolithographic methods of etching substrates are particularly well suited for the microfabrication of these substrates and are well known in the art. For example, the first sheet of a substrate may be overlaid with a photoresist. An electromagnetic radiation source may then be shone through a photolithographic mask to expose the photoresist in a pattern which reflects the pattern of chambers and/or channels on the surface of the sheet. After removing the exposed photoresist, the exposed substrate may be etched to produce the desired wells and channels. Generally preferred photoresists include those used extensively in the semiconductor industry. Such materials include polymethyl methacrylate (PMMA) and its derivatives, and electron beam resists such as poly (olefin sulfones) and the like (more fully discussed in, e.g., Ghandi, "VLSI Fabrication Principles," Wiley (1983) Chapter 10, incorporated herein by reference in its entirety for all purposes).

The planar members are bonded together or laminated to produce a fluid tight body of the device. Bonding of the planar members of the device may generally be carried out using a variety of methods known in the art and which may vary depending upon the materials used. For example, adhesives may generally be used to bond the planar members together. Where the planar members are, e.g., glass, silicon or combinations thereof, thermal bonding, anodic/electrostatic or silicon fusion bonding methods may be applied. For polymeric parts, a similar variety of methods may be employed in coupling substrate parts together, e.g., heat with pressure, solvent based bonding. Generally, acoustic welding techniques are generally preferred. In a related aspect, adhesive tapes may be employed as one portion of the device forming a thin wall of the reaction chamber/channel structures.

In additional embodiments, the body may comprise a combination of materials and manufacturing techniques described above. In some cases, the body may include some parts of injection molded plastics, and the like, while other portions of the body may comprise etched silica or silicon planar members, and the like. For example, injection molding techniques may be used to form a number of discrete cavities in a planar surface which define the various reaction chambers, whereas additional components, e.g., fluid channels, arrays, etc, may be fabricated on a planar glass, silica or silicon chip or substrate. Lamination of one set of parts to the other will then result in the formation of the various reaction chambers, interconnected by the appropriate fluid channels.

In particularly preferred embodiments, the body of the device is made from at least one injection molded, press molded or machined polymeric part that has at least one or more features or depressions manufactured into its surface to define a bubble removing mechanism. Molds or mold faces for producing these injection molded parts may generally be fabricated using the methods described herein for, e.g., conventional machining or silicon molds. Examples of suitable polymers for injection molding or machining include, e.g., polycarbonate, polystyrene, polypropylene, polyethylene, acrylic, and commercial polymers such as Kapton, Valox, Teflon, ABS, Delrin and the like. A second part that is similarly planar in shape is mated to the surface of the polymeric part to define the remaining wall of the bubble removing mechanism(s). Published PCT Application No. 95/33846, incorporated herein by reference, describes a device that is used to package individual oligonucleotide arrays. The device includes a hybridization chamber disposed within a planar body. The chamber is fluidly connected to an inlet port and an outlet port via flow channels in the body of the device. The body includes a plurality of injection molded planar parts that are mated to form the body of the device, and which define the flow channels and hybridization chamber.

The surfaces of the bubble removing mechanism which contact the samples and reagents may also be modified to better accommodate a desired reaction. Surfaces may be made more hydrophobic or more hydrophilic depending upon the particular application. Alternatively, surfaces may be coated with any number of materials in order to make the overall system more compatible to the reactions being carried out. For example, in the case of nucleic acid analyses, it may be desirable to coat the surfaces with a non-stick coating, e.g., a Teflon, parylene or silicon, to prevent adhesion of nucleic acids to the surface. Additionally, insulator coatings may also be desirable in those instances where electrical leads are placed in contact with fluids, to prevent shorting out, or excess gas formation from electrolysis. Such insulators may include those well known in the art, e.g., silicon oxide, ceramics or the like.

The device of the present invention is generally capable of carrying out a number of preparative and analytical reactions on a number of samples. Most assays often require multiple reagents to be added sequentially. Entrapped air between reagents needs to be removed in order to have multiple liquids or fluid segments merge together. According to an embodiment of the present invention, to achieve this end, the device generally comprises at least one inlet channel, a bubble removing chamber, a venting channel and a set of control valves within a single unit or body. According to an embodiment of the present invention, surface tension is utilized to maintain the liquid in the desired location and allow entrapped air to leak out.

According to one aspect of the present invention, a system for introducing multiple reagents and adding them sequentially is provided as shown in FIG. 1. This diagram is merely an example, which should not unduly limit the scope of the claims. One of ordinary skill in the art would recognize many variations, alternatives, and modifications. According to a preferred embodiment of the present invention, a system for adding multiple reagents sequentially without entrapment of air is provided that includes a housing comprising a fluid cavity, wherein the fluid cavity comprises at least one main channel having a neighboring channel of a different depth aligned longitudinally connected to a venting channel. The abrupt change in surface between the channels of varying depth is such that the surface tension of the main channel maintains the fluid in contact, allowing entrapped air to dispel through the neighboring hollow channel.

FIG. 1 illustrates a preferred embodiment of an overall layout of a system of channels of inlets (101), inlet channels (102), a main channel (103), vents (104), venting channels (105), outlet (106), outlet channels (107), and a plurality of various configurations of bubble removing mechanisms. A different fluid is introduced from each inlet (101). In this preferred embodiment, as indicated in FIG. 1, four different bubble removing mechanism configurations: first (110), second (111), third (112) and fourth (113) is provided. Each bubble removing mechanism is connected to a venting channel (105). The alignment pins (120) assure that the substrates that create the system are held together and aligned with each other.

According to an embodiment of the present invention, a method for removing a bubble is provided where multiple fluids are introduced sequentially in the apparatus shown in FIG. 1. In a preferred embodiment, a first fluid of a desired volume is introduced into the inlet (101) and into the main channel (103). Then sequentially another fluid of a desired volume is introduced from a different inlet (101), creating an air pocket or bubble in between the first fluid and the second fluid. A mechanism, for example a pressurized gas, moves the fluids wherein a bubble is in between the first fluid and the second fluid through the main channel (103). As the fluids pass through the main channel and a bubble removing mechanism, the bubble is dispelled into the hollow part of the channel while the surface tension maintains the fluid in the main channel. In another embodiment of the present invention, a number of various fluids are added sequentially based on this method with each bubble being dispelled in each bubble removing mechanism while the fluids are being collected through the outlet (106) into a chamber (not shown).

Figure 2B:
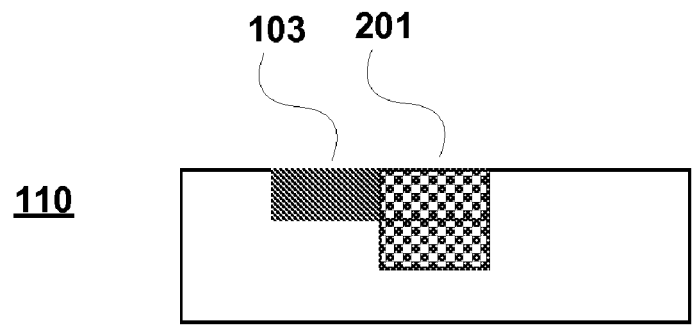
FIGS. 2b-2e illustrate examples of preferred embodiments of the various channel designs.
Figure 2C:
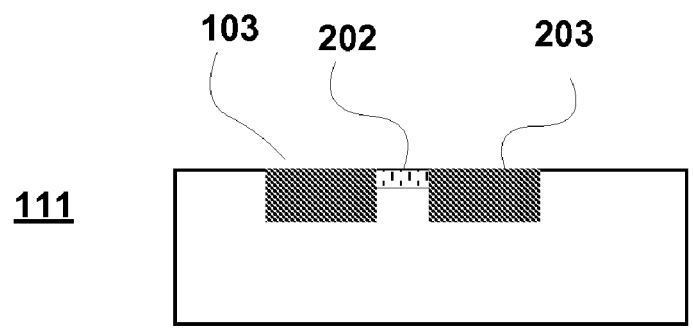
Figure 2D:
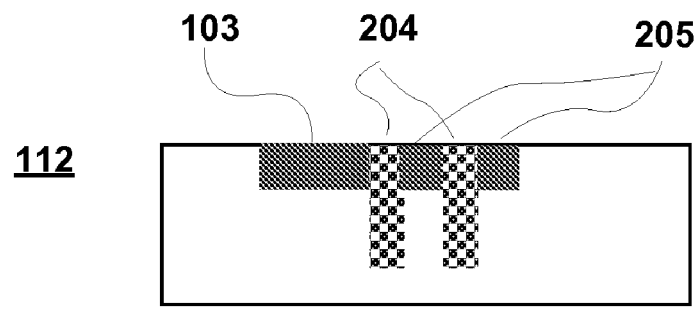

FIGS. 2a-2e illustrate further details of the system of the bubble removing channels shown in FIG. 1 according to an embodiment of the present invention. FIG. 2a illustrates a legend for the various depths of the bubble removing mechanisms. In this example, the depths of the channels are specified as 200 μm, 400 μm and 20 μm in depth. In a preferred embodiment, the depth is generally in the range of 10 to 2,000 μm, more preferably 10 to 1,000 μm and most preferably 20 to 500 μm. FIGS. 2b-2e illustrate examples of preferred embodiments of the present invention of various channel designs of a bubble removing mechanism. These diagrams are merely examples, which should not unduly limit the scope of the claims. One of ordinary skill in the art would recognize many variations, alternatives, and modifications. FIG. 2b illustrates the first channel design of a bubble removing mechanism (110) which includes the main channel (103) and a neighboring bubble removing channel that is 400 μm in depth (201). FIG. 2c illustrates the second channel design of a bubble removing mechanism (111) which includes the main channel (103) and two neighboring bubble removing channels that are 20 μm (202) and 200 μm (203) in depths. FIG. 2d illustrates the third channel design of a bubble removing mechanism (112) which includes the main channel (103) and four neighboring bubble removing channels that are alternating channels of 400 μm (204) and 200 μm (205) in depths.

Figure 2E:
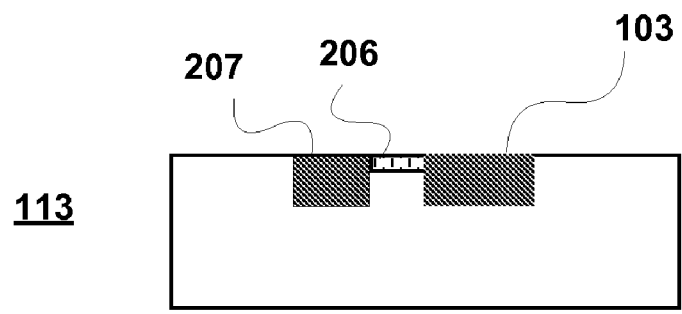

FIG. 2e illustrates the forth channel design of a bubble removing mechanism (113) which includes the main channel (103) and two neighboring bubble removing channels that are 20 μm (206) and 200 μm (207) in depth wherein the 20 μm channel is disconnected in the middle section as shown in FIG. 1.

FIGS. 3 and 4 illustrate alternative embodiments of the present invention, of various physical shapes and configuration of the bubble removing mechanism. FIG. 3a illustrates the main channel (103) and the design of the neighboring bubble removing mechanism which is rectangular in shape (301). FIG. 3b illustrates a side view of the channel design indicating the middle section of the main channel (103) not being opened to the bubble removing mechanism (301). While the fluid (304) moves forward (302) in the main channel, the gas or air is dispelled (303) across the hollow channel (301) while the surface tension of the main channel maintains the fluid. FIG. 3c illustrates the appearance of the shape of the fluid (304) in the rectangular shaped bubble removing mechanism (301).

Figure 4A:
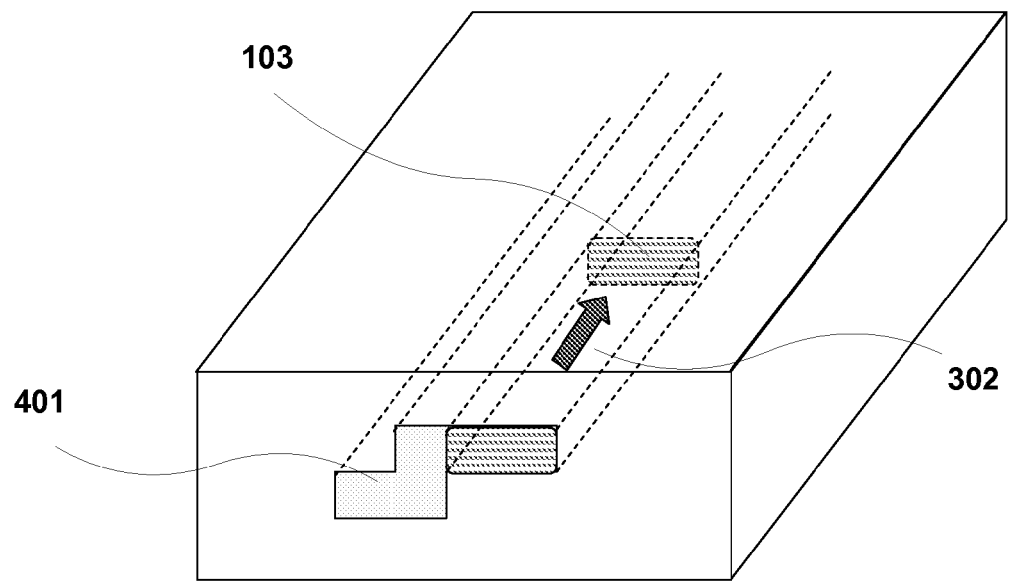
FIG. 4a illustrates the channel design where the bubble removing mechanism is in the shape of an "L" and located at the side of the main channel.
Figures 4B, 4C:
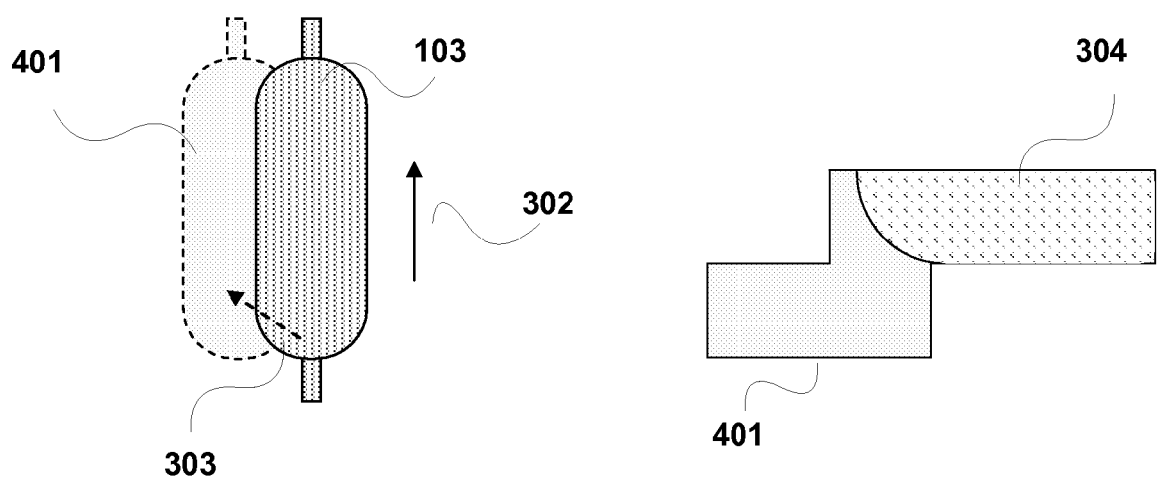
FIG. 4b illustrates a side view of the channel design indicating the shapes of the overall channels.
FIG. 4c illustrates the appearance of the shape of the fluid in the channel.

FIG. 4a illustrates the main channel (103) and the design of the neighboring bubble removing mechanism which is in the shape of an "L" (401). FIG. 4b illustrates a side view of the channel design indicating the shapes of the overall channels. While the fluid (304) moves forward (302) in the main channel, the gas or air is dispelled (303) across the hollow channel (401) while the surface tension of the main channel maintains the fluid. FIG. 4c illustrates the appearance of the shape of the fluid (304) in the rectangular shaped bubble removing mechanism (401).

Figure 5:
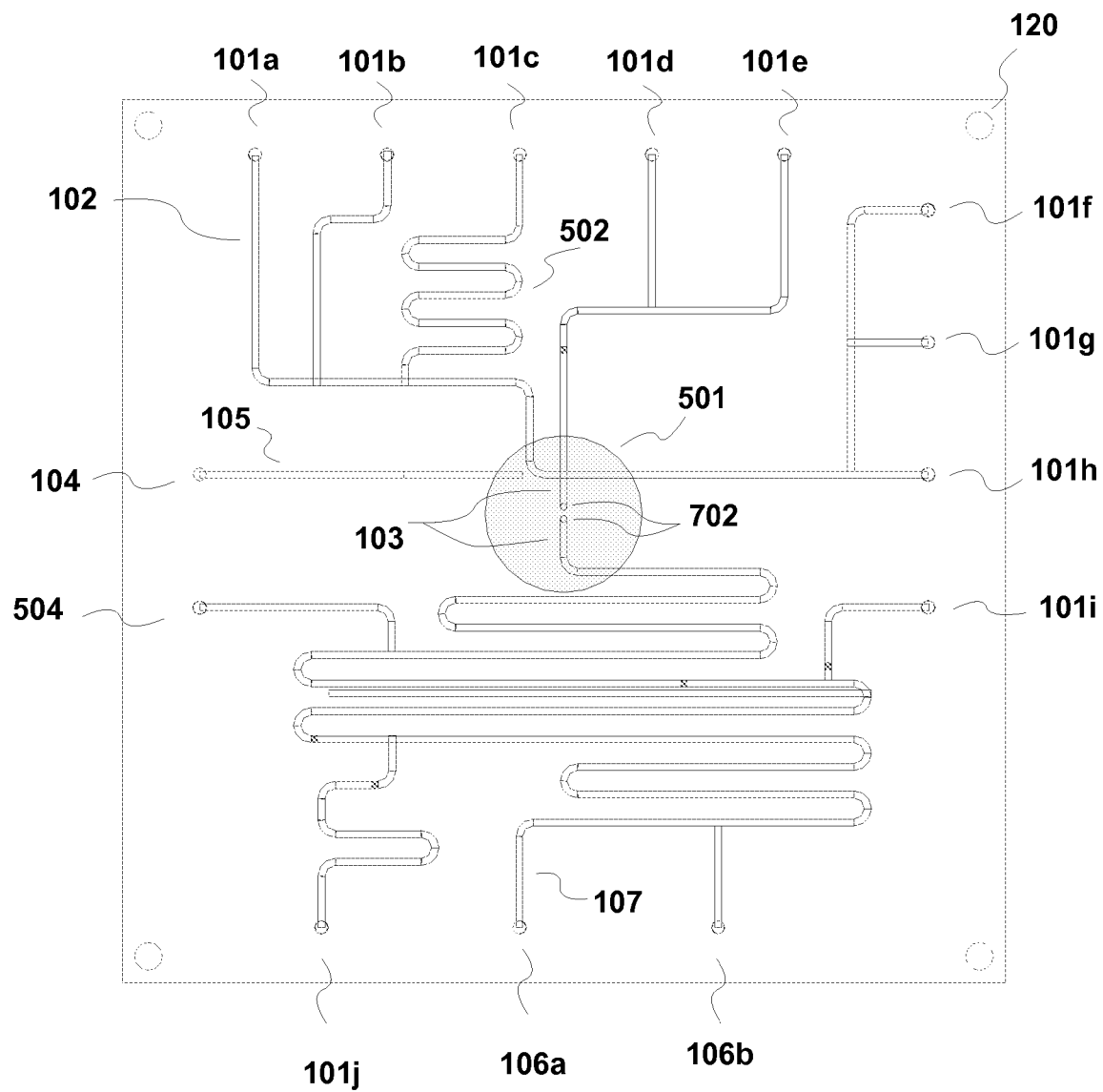
FIG. 5 illustrates an alternative embodiment of a system of channels for introducing multiple samples and performing a number of reactions and steps with an alternative bubble removing mechanism according to an embodiment of the present invention.

According to one aspect of the present invention, a system for introducing multiple samples and performing multiple reactions and steps using surface tension inside a chamber to hold a liquid and allow entrapped air to leak out is provided as illustrated in FIG. 5. This diagram is merely an example, which should not unduly limit the scope of the claims. One of ordinary skill in the art would recognize many variations, alternatives, and modifications. FIG. 5 illustrates another preferred embodiment of an overall layout of a system of channels of inlets (101), inlet channels (102), a main channel (103), vents (104), venting channels (105), outlets (106), outlet channels (107), and a central bubble removing mechanism configuration (501) according to a preferred embodiment of the present invention. In another embodiment of the present invention, the shape of the chamber (i.e. top view) is a circle, a trapezoid, a oval, a triangle, or another shape one of ordinary skill in the art would recognize. The example of the circular chamber type of a bubble remove mechanism is merely an example, which should not unduly limit the scope of the claims. One of ordinary skill in the art would recognize many variations, alternatives, and modifications, for example, other types of shape, location, and the quantity. According to another embodiment of the present invention, the apparatus includes three machined or injection molded polymeric substrates: first (601), second (701), and third (801) layers as shown in FIG. 6, FIG. 7 and FIG. 8 respectively. The alignment pins (120) assure that the substrates that create the system are held together and aligned with each other.

According to one aspect of the present invention, systems, methods, and computer software products are provided for bubble removal and sample preparation of biological assays. Merely by way of example, the invention is described as it applies to preparing nucleic acid samples for hybridization with microarrays but it should be recognized that the invention has a broader range of applicability. According to an embodiment of the present invention, the inlets (101) in the system as shown in FIG. 5 are used for introduction of the following: Primer annealing mix (101a), 1$^{st}$ strand synthesis (101b), 2$^{nd}$ strand synthesis (101c), gas inlet (101d), T4 DNA polymerase (101e), EDTA (101f), Beads (101g), EB buffer (101h), Fragmentation (101i), and Labeling (101j). According to another embodiment of the present invention, the channel design is, for example, curved (101c) to provide an area to hold a larger volume of reagent to be placed into the chamber type bubble removing mechanism (501) as desired for the 2$^{nd}$ strand synthesis process step. The air vent (104) is connected to the central chamber bubble removing mechanism (501). According to another embodiment of the present invention, mixing is performed by using air pressure to move the fluids back and forth in the, for example, curved channel. Elastomeric valves are opened and closed by application of vacuum or pressure (approx. 60 psi) to the space above the individual valves. In a preferred embodiment, a waste port (101k) is used to remove unwanted fluids and at the end of the process, a collection port (106) collects the processed fluids.

Figure 6A:
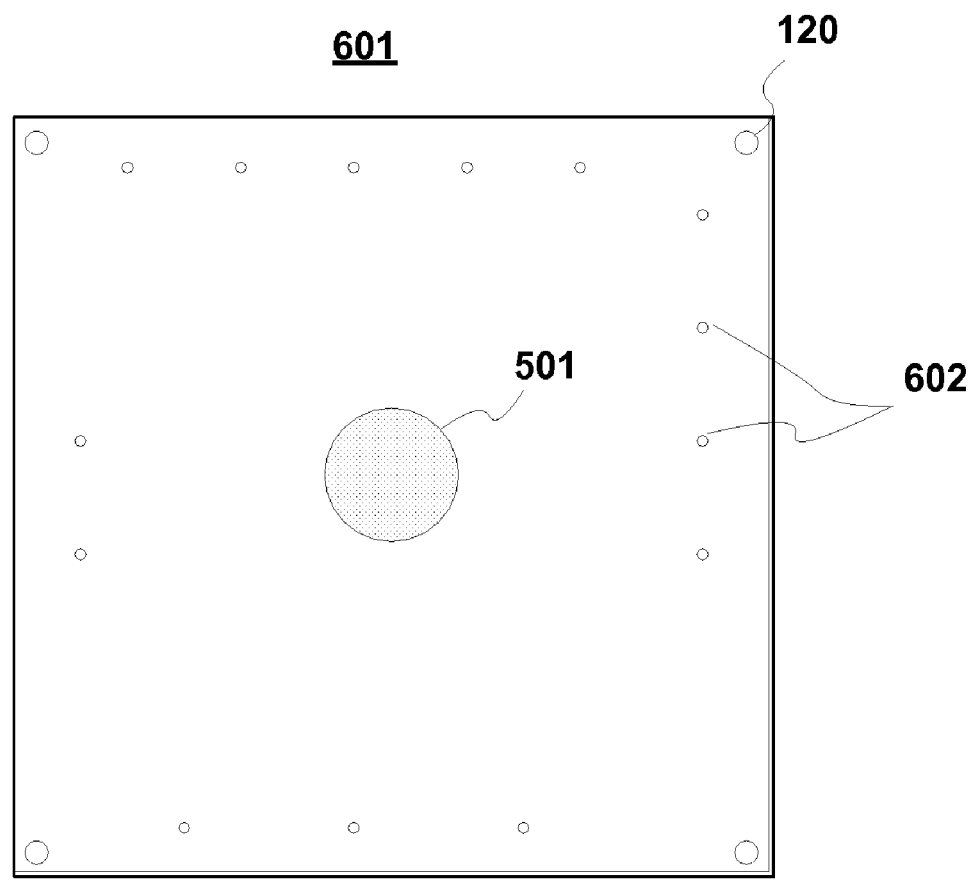
FIG. 6a illustrates the top view of the first substrate and FIG. 6b illustrates the side view of the first substrate of the system illustrated in FIG. 5.
Figure 6B:
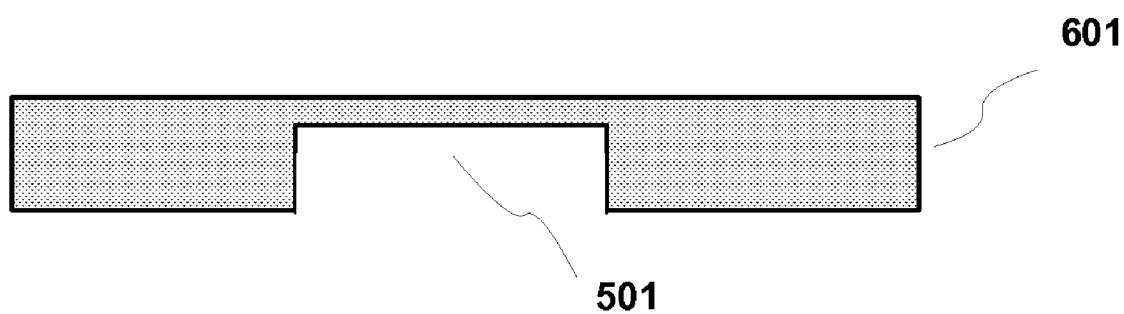

FIG. 6 illustrates another preferred embodiment of the first substrate (601) of the system as described in FIG. 5. In a preferred embodiment, the first substrate (601) includes a central chamber type bubble removing mechanism (501) as shown in FIG. 6a (top view) and in FIG. 6b (side view). The first substrate (601) includes holes (602) according to an embodiment of the present invention corresponding to the holes in second substrate (701). These holes my be the ends of the channels on the second and third substrate (801). The depth of the chamber of the central chamber type bubble removing mechanism (501) depends on several factors, for example, the volume requirement of the process step(s).

Figure 7A:
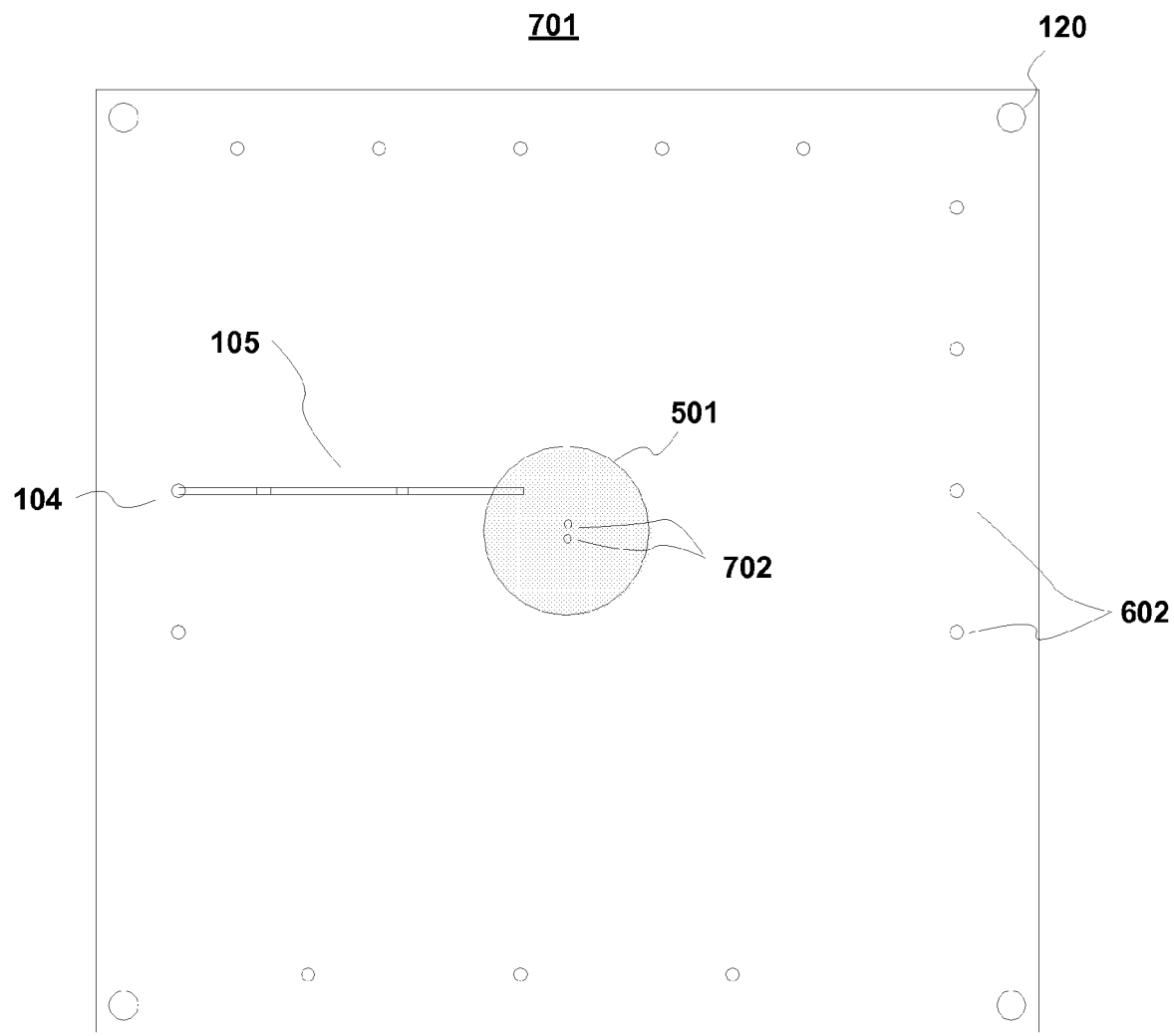
FIG. 7a illustrates the top view and FIG. 7b illustrates the side view of the second substrate of the system illustrated in FIG. 5.
Figure 7B:
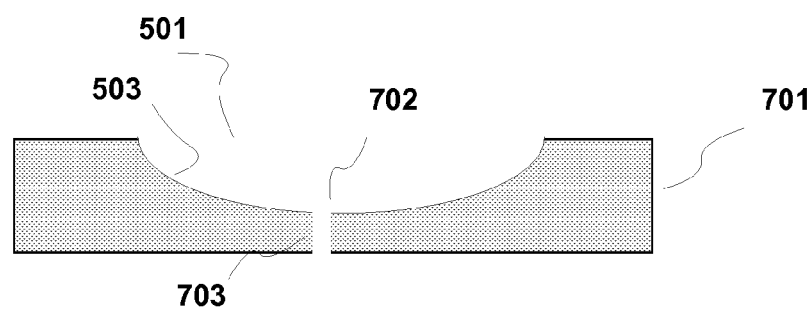

FIG. 7 illustrates another preferred embodiment of the second substrate (701) of the system as described in FIG. 5. In a preferred embodiment, the second substrate (701) includes a central chamber type bubble removing mechanism (501) as shown in FIG. 7a (top view) and in FIG. 7b (side view). In a preferred embodiment of the present invention, the chamber (501) is adapted with a first radius (503) to retain a quantity of fluid. The radius (503) of the bottom surface of the chamber type bubble removing mechanism (501) is in the range of 1 to 20 mm, preferably in the range of 2 to 10 mm, and most preferred in the range of 1 to 2 mm.

The second substrate (701) includes holes (602) according to an embodiment of the present invention corresponding to the holes in first substrate (601), and the ends of the channels on the third substrate (801). In a preferred embodiment of the present invention, there are also two chamber entrance holes (702) connecting to the chamber channels (703) shown in FIG. 7b which are then connected to the corresponding main channels (103) in the third substrate (801).

Figure 7C:
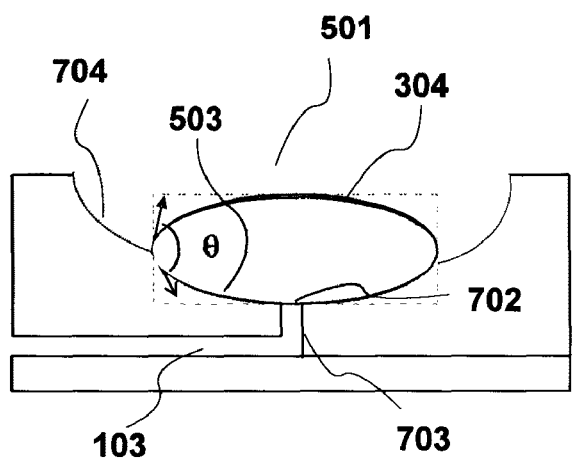
FIG. 7c illustrates the side view of a bubble removing mechanism with a collected fluid according to an embodiment of the present invention.
Figure 8:
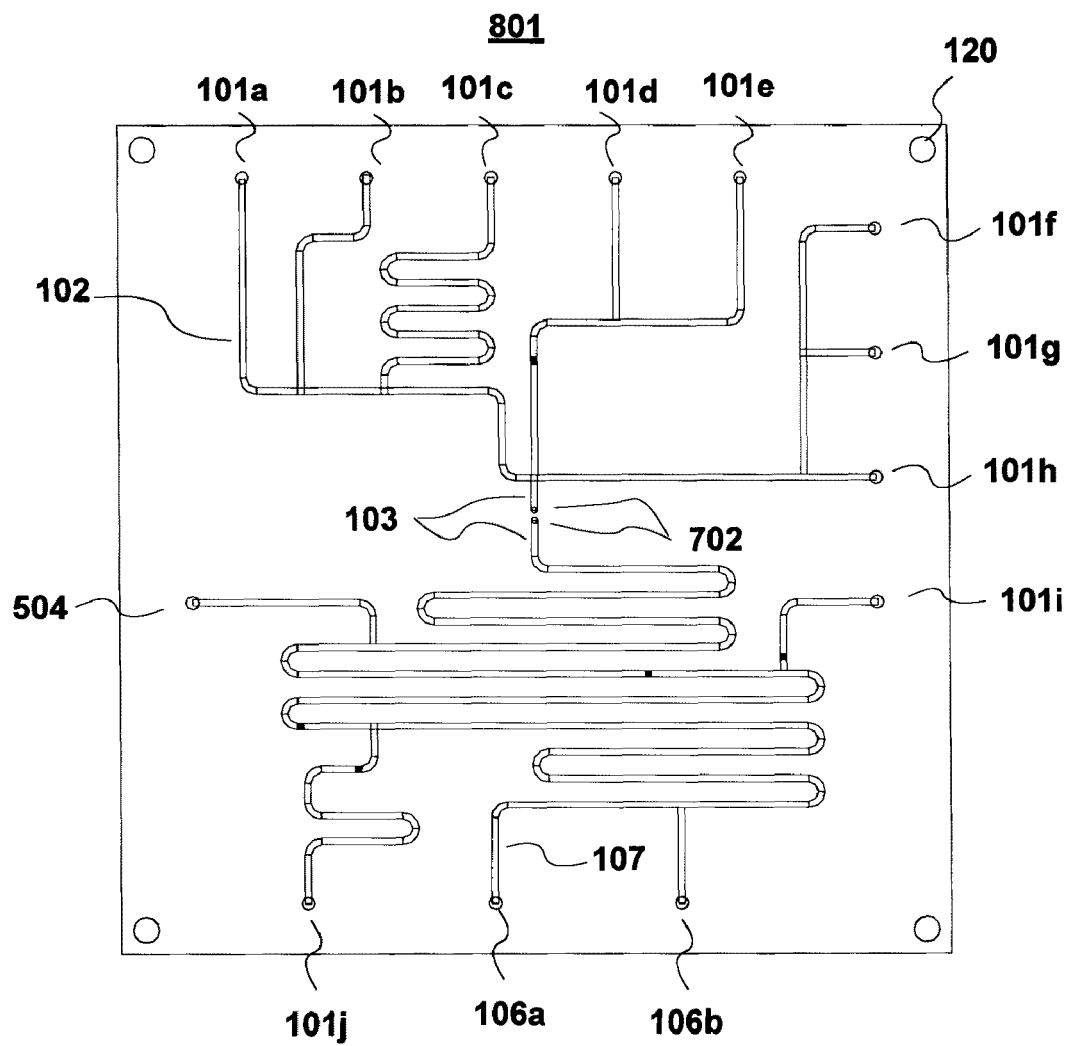
FIG. 8 illustrates the top view of the third substrate of the system illustrated in FIG. 5 according to an embodiment of the present invention.

FIG. 7c illustrates another preferred embodiment of the present invention of the configuration of the chamber type bubble removing mechanism (501). According to a preferred embodiment of the present invention, the chamber (501) is adapted with a first radius (503) and a second radius (704) to retain a quantity of fluid. The second radius of the bottom surface of the chamber type bubble removing mechanism (501) is in the range of 1 to 20 mm, preferably in the range of 2 to 4 mm, and most preferred in the range of 1 to 2 mm.

In another embodiment of the present invention, the number of stages can vary from 1 to 8 stages, preferably 1 to 4, and most preferable 1 to 2 stages. The two stage circular chamber described in FIG. 7c is merely an example, which should not unduly limit the scope of the claims. The additional stages include, for example, increased cross sections. One of ordinary skill in the art would recognize many variations, alternatives, and modifications.

FIG. 8 illustrates another preferred embodiment of the third substrate (801) of the system as described in FIG. 5. In a preferred embodiment, the third substrate (801) includes an overall layout of a system of channels of inlets (101), inlet channels (102), a main channel (103), vents (104), venting channels (105), outlets (106), and outlet channels (107) according to a preferred embodiment of the present invention. The third substrate (801) includes chamber entrance holes (702) according to an embodiment of the present invention corresponding to the holes in second substrate (701) leading into the bottom of the chamber type bubble removing mechanism (501). The two entrance holes to the chamber described in FIG. 8 is merely an example, which should not unduly limit the scope of the claims. The number of entrance holes to the chamber will depend on the application of the lab card.

The alignment pins (120) assure that the three substrates are aligned after the parts are mated together. According to an embodiment of the present invention, an apparatus for removing a bubble is provided which includes a first substrate (601) having an inner surface that defines a top surface of at least one chamber (501), a second substrate (701) having inner surfaces that define the chamber (501) and a venting channel (105) there between the first substrate (601) and the second substrate (701), and a third substrate (801) having inner surfaces that define at least one main channel (103) leading into a bottom entrance of the chamber (501) connected to a bottom surface of the chamber (501) in the second substrate (701). The bottom surface of the chamber (501) is coated to provide a hydrophobic surface. In addition, the bottom surface of the chamber is adapted with a radius to retain a quantity of a first fluid and a second fluid such that the surface tension of the bottom surface maintains the fluids in contact with the bottom surface of the chamber. A pressurized gas is used for moving the fluids. As the fluids are collected into the chamber, the bubble between the first fluid and the second fluid is dispelled in the chamber resulting in the removal of the bubble from the fluids.

The chamber includes a radius such that the surface tension of the bottom surface of the chamber maintains the fluid in contact with the bottom surface of the chamber. In a preferred embodiment of the present invention, the chamber is adapted with a first radius to retain a quantity of fluid. The first radius of the bottom surface of the chamber is in the range of 1 to 20 mm, preferably in the range of 2 to 10 mm, and most preferred in the range of 2 to 4 mm. According to another preferred embodiment of the present invention, the apparatus described above is provided with a second radius to further assure the retention of the fluids at the bottom of the chamber while the bubble is being removed. In a preferred embodiment, the second radius is in the range of 1 mm to 20 mm, more preferably 2 mm to 4 mm and most preferably 1 mm to 2 mm.

In an alternative embodiment, the apparatus for removing bubbles has multiple inlet channels leading to the chamber channel as illustrated in FIG. 9. These diagrams are merely examples, which should not unduly limit the scope of the claims. One of ordinary skill in the art would recognize many variations, alternatives, and modifications. There are several ways that the channels and chamber can be created. For example, in FIG. 5, majority of the depths of the channels are in the third substrate, however, in FIG. 9, the depths of the channels are in the second substrate (701). The apparatus includes a first substrate (610) which is not shown, a second substrate (701) having inner surfaces that define a plurality of main channels (103) leading to a chamber channel (501) and a third substrate (801). In this example, the second substrate (701) includes the depths of the channels and the chamber and the third substrate (801) provides a surface to create the bottom surface of the channels. The main channels (103) are connected to the chamber channel (703), which is connected to the chamber entrance holes (702) which are located at the bottom of the chamber type bubble removing mechanism (501). The bottom surface of the chamber (501) is adapted with a radius (503) to retain a quantity of fluid. The radius (503) is such that the surface tension of the bottom surface of the chamber maintains the fluid in contact with the bottom surface of the chamber.

FIG. 9 illustrates an example where there are two main channels (103) leading to the chamber channel (703). Depending on which channel is used to introduce the fluid, the other channel is blocked such that the fluid is directed into the chamber. One of ordinary skill in the art would recognize many ways to providing a block (901) to a vented channel. FIG. 9a illustrates the introduction of a first fluid (304) of a desired volume from the first inlet (1011), to the chamber type bubble removing mechanism (501), while the second inlet (101m) is blocked (901). The chamber type bubble removing mechanism (501) has a radius (503) such that the surface tension of the bottom surface of the chamber maintains the fluid in contact with the bottom surface of the chamber. In a preferred embodiment of the present invention, the chamber (501) is adapted with a first radius (503) to retain a quantity of fluid. The first radius (503) of the bottom surface of the chamber type bubble removing mechanism (501) is in the range of 1 to 20 mm, preferably in the range of 2 to 10 mm, and most preferred in the range of 2 to 4 mm. According to a preferred embodiment of the present invention, the apparatus described above is provided with a second radius (704) to further assure the retention of the fluids at the bottom of the chamber while the bubble is being removed. In a preferred embodiment, the second radius (704) is in the range of 1 mm to 20 mm, more preferably 2 mm to 4 mm and most preferably 1 mm to 2 mm.

According to an embodiment of the present invention, a protective coating such as a hydrophilic or hydrophobic coating (depending upon the nature of the fluid or solvent) is utilized over portions of the substrate to be protected, sometimes in combination with materials that facilitate wetting by the reactant solution in other regions. In this manner, the flowing solutions are further prevented from passing outside of their designated flow paths. In one preferred embodiment of the present invention, the bottom surface of the chamber type bubble removing mechanism (501) is coated with a hydrophobic coating. One of skill in the art will recognize that there are alternative methods of forming channels or otherwise protecting a portion of the surface of the substrate.

Figure 9A:
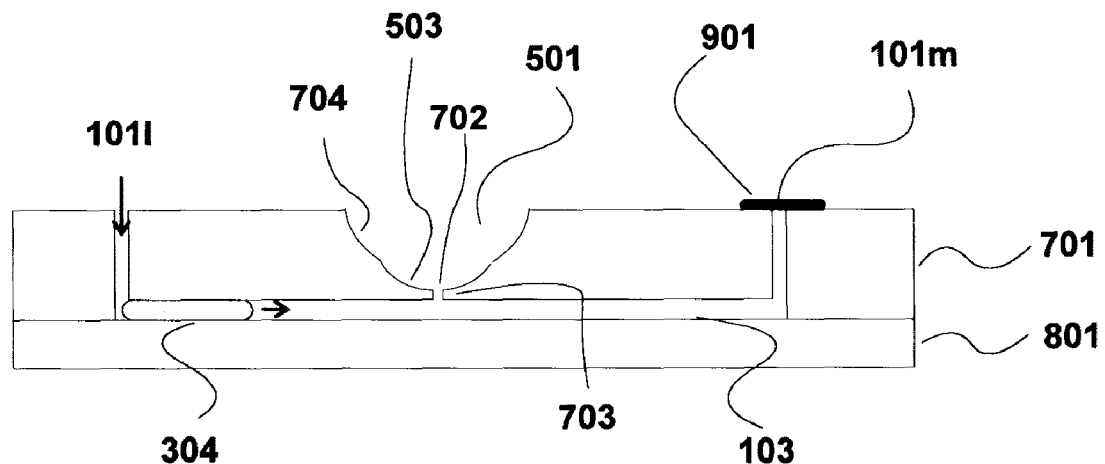
FIG. 9a indicates the first step of introducing a first fluid.
Figure 9B:
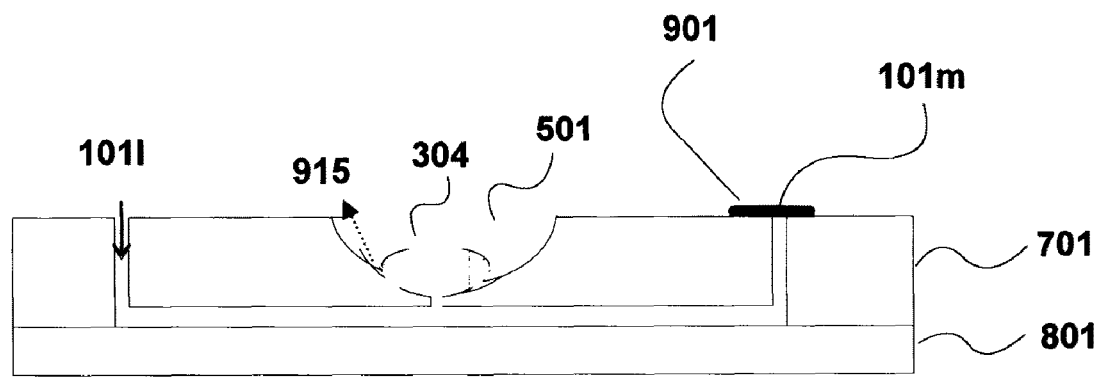
FIG. 9b indicates where the first fluid is collected in the chamber.
Figure 9C:
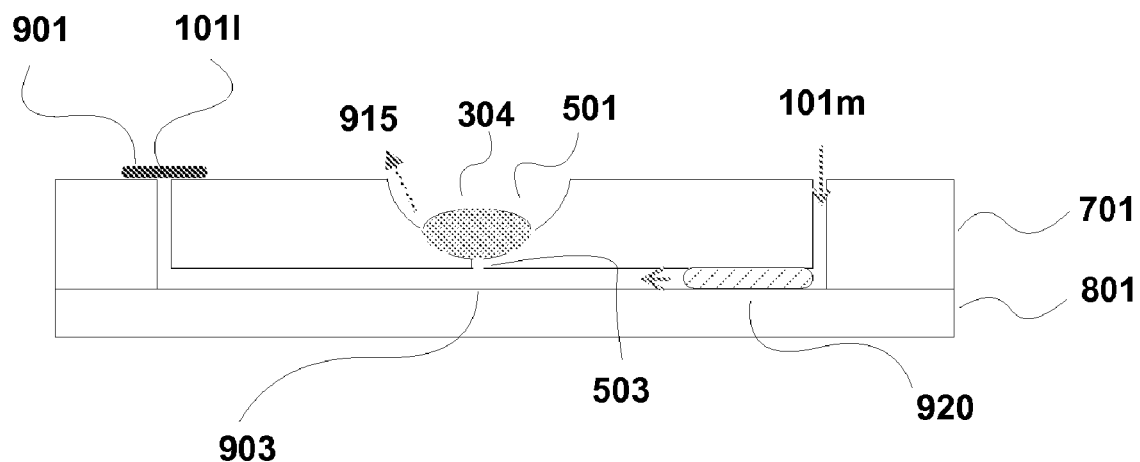
FIG. 9c indicates the next step where the second fluid is introduced.
Figure 9D:
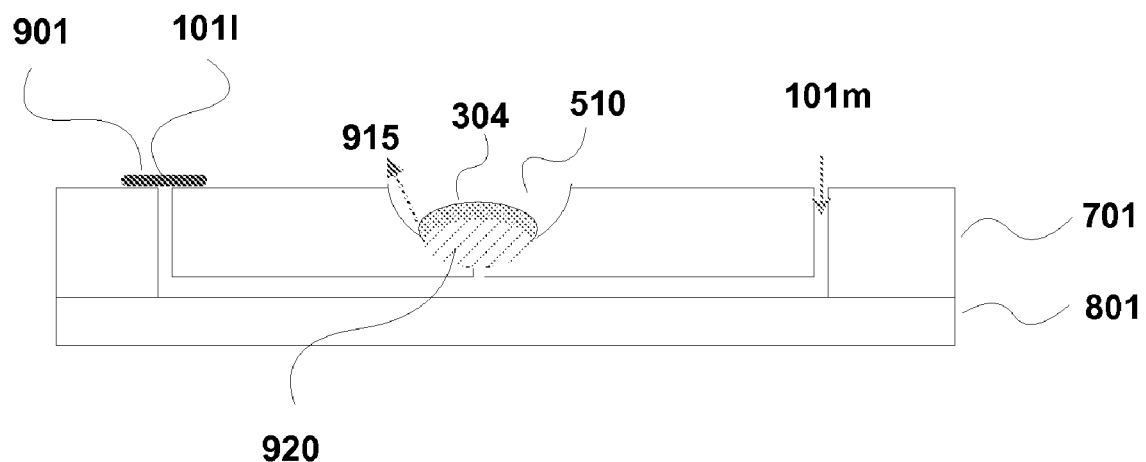
FIG. 9d indicates the air or gaseous bubble being dispelled while the second fluid is collected into the chamber.

FIG. 9b illustrates the fluid (304) in the chamber type bubble removing mechanism (501) while any excess air dissipates (915) through the sides of bubble which remains in contact with the bottom surface of the chamber based on surface tension. FIG. 9c illustrates the next step where the second fluid (920) of a desired volume is introduced from the second inlet (101m), while the other inlet channel (101l) is blocked (901). FIG. 9d illustrates the collection of the two fluids in the chamber type bubble removing mechanism (501) as any excess air or air bubbles are dispelled (915) through the sides of the bubble.

According to another embodiment of the present invention, a method for removing a bubble is provided where multiple fluids are introduced into a common main channel (103) for example, as shown in FIG. 5. In another embodiment of the present invention, additional fluids are added sequentially based on this method with each bubble being dispelled in the chamber while the fluids are being collected in the chamber. In a preferred embodiment, a first fluid (304) of a desired volume is introduced into the main channel (103) from the first inlet, for example, (101a) and then another fluid (920) of a desired volume is introduced from another inlet (101b), and then another inlet, for example, (101c-101h), creating an air pocket or bubble in between the first fluid (304) and the following fluids. The number of fluids to be introduced sequentially into the chamber type bubble removing mechanism (501) will depend on several factors, for example, the size of the chamber and the process step requirements. A mechanism, for example, a pressurized gas moves the fluids wherein a bubble is in between a fluid and the next fluid through the main channel (103) into the chamber (501). The fluids are collected in the chamber while the bubble is dispelled through the sides of the chamber where the bubble is in contact with the bottom surface of the chamber.

According to another embodiment of the present invention, a method for removing a pre-existing bubble is provided, where a bubbles is in a fluid. The mixing process can be performed by applying positive and negative pressure in a mixing channel alternatively in each cycle. The fluid with the bubble is moved back and forth for a number of times using a mixing mechanism until the bubble is forced to the end of the liquid according to an embodiment of the present invention. According to another embodiment of the present invention, after the bubble is forced to an end of the liquid segment, the bubble removing mechanism described above can then be use to dissipate the bubble.

Figure 10A:
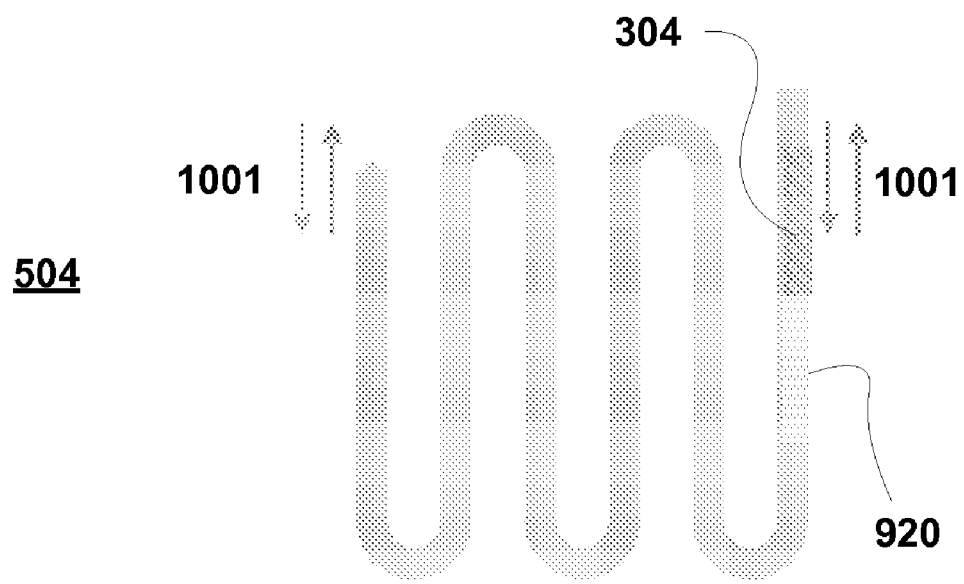
FIG. 10a illustrates the initial phase of the mixing process.
Figure 10B:
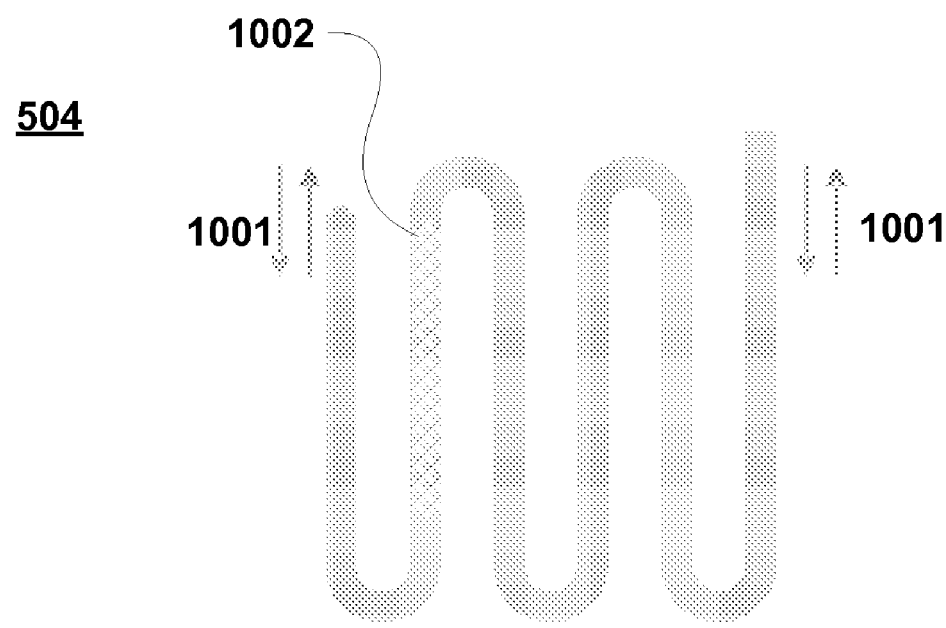
FIG. 10b illustrates the final phase of the mixing process.

According to an embodiment of the present invention, the mixing mechanism (504) described above can also be use to a plurality of fluids, for example, a first fluid (304) and a second fluid (920) as illustrated in FIG. 10a. In general, the mixing of the liquid segments is based on the Taylor Dispersion Theory in laminar flow. Thorough mixing is achieved, for example, by using a longer mixing channel and performing more cycles to achieve the desired mixed solution as shown in FIG. 10b.

All the diagrams in this application are merely examples, which should not unduly limit the scope of the claims. One of ordinary skill in the art would recognize many variations, alternatives, and modifications.

IV. Applications

The various bubble removing systems set forth in the present invention, including those made from polycarbonate, polypropylene, silicon and glass and coated with parylene, silicone, and silicon nitride of the present invention may be used in microfluidic devices for a variety of enzymatic reactions.

For example, the microfluidic devices that can utilize a bubble removing system according to the present invention are devices that carry out RNA polymerization, i.e., reverse and in vitro transcription. In other embodiments, RNA modification has been carried out in microfluidic devices, such as Poly A polymerase (AMP added to 3' end of RNA, can be used for labeling), polynucleotide kinase (transfer gamma-phosphate of ATP to 5' of DNA or RNA, can be used for labeling) and alkaline phosphatase (removes free 5'OH). RNA fragmentation, such as RNA-DNA duplex nicking (e.g., RNAase H) and RNAase digestion has also been carried out.

In other embodiments of the present invention, DNA polymerization can be carried out with the microfluidic devices that can utilize a bubble removing system according to the present invention. Examples of such polymerization include isothermal amplification (NASBA, 3SR, etc), PCR amplification (deep vent, amplitaq gold, taq) and cycle sequencing amplification (with labeled dideoxy terminators, or with labeled primers (e.g., energy transfer dyes). In addition, DNA modification, such as terminal deoxy-transferase (TdT), ligation (including chimeric ligation with RNA) and alkaline phosphatase (removes free 5'OH). Other DNA applications includes DNA fragmentation, such as double stranded DNA (DNAase or restriction endonucleases) or single stranded DNA (nuclease SI) and peptide manipulation, such as in vitro translation and protease digestion.

The device and system of the present invention has a wide variety of uses in the manipulation, identification and/or sequencing of nucleic acid samples. These samples may be derived from plant, animal, viral or bacterial sources. For example, the device and system of the invention may be used in diagnostic applications, such as in diagnosing genetic disorders, as well as diagnosing the presence of infectious agents, e.g., bacterial or viral infections. Additionally, the device and system may be used in a variety of characterization applications, such as gene expression, forensic analysis, e.g., genetic fingerprinting, bacterial, plant or viral identification or characterization, e.g., epidemiological or taxonomic analysis, and the like.

Although generally described in terms of individual devices, it will be appreciated that multiple devices may be provided in parallel to perform analyses on a large number of individual samples since the devices are miniaturized and reagent and/or space requirements are substantially reduced. Similarly, the small size allows automation of sample introduction process using, e.g., robot samplers and the like.

In preferred aspects, the apparatus, method and system of the present invention is used in devices for analysis of human samples. More particularly, the device is used to determine the presence or absence of a particular nucleic acid sequence within a particular human sample. This includes the identification of genetic anomalies associated with a particular disorder, as well as the identification within a sample of a particular infectious agent, e.g., virus, bacteria, yeast or fungus.

The apparatus, method and system of the present invention is used in devices may also be used in de novo sequencing applications. In particular, the apparatus, method and system may be used in sequencing by hybridization (SBH) techniques. The use of oligonucleotide arrays in de novo SBH applications is described, for example, in U.S. patent application Ser. No. 08/082,937, filed Jun. 25, 1993.

According to an embodiment of the present invention, an apparatus, a method and a system for removing a bubble are provided which includes a first substrate having an inner surface that defines a top surface of at least one chamber, a second substrate having inner surfaces that define the chamber and at least one venting channel there between the first substrate and the second substrate, and a third substrate having inner surfaces that define at least one main channel leading into a bottom entrance of the chamber connected to a bottom surface of the chamber in the second substrate. The bottom surface of the chamber is coated to provide a hydrophobic surface. In addition, the bottom surface of the chamber is adapted with a radius to retain a quantity of a first fluid and a second fluid such that the surface tension of the bottom surface maintains the fluids in contact with the bottom surface of the chamber. A pressurized gas is used for moving the fluids. As the fluids are collected into the chamber, the bubble between the first fluid and the second fluid is dispelled in the chamber resulting in the removal of the bubble from the fluids.

The chamber includes a radius such that the surface tension of the bottom surface of the chamber maintains the fluid in contact with the bottom surface of the chamber. In a preferred embodiment of the present invention, the chamber is adapted with a first radius to retain a quantity of fluid. The first radius of the bottom surface of the chamber is in the range of 1 to 20 mm, preferably in the range of 2 to 10 mm, and most preferred in the range of 2 to 4 mm. According to another preferred embodiment of the present invention, the apparatus described above is provided with a second radius to further assure the retention of the fluids at the bottom of the chamber while the bubble is being removed. In a preferred embodiment, the second radius is in the range of 1 mm to 20 mm, more preferably 2 mm to 4 mm and most preferably 1 mm to 2 mm. According to another preferred embodiment of the present invention, an apparatus is provided wherein the venting channel is at a different location.

EXAMPLES

Example 1

Demonstration of Bubble Removing System

A polycarbonate cartridge was fabricated using conventional machining, forming an array of valves linking a series of channels to a bubble removing chamber which was connected to a venting channel. Elastomeric valves were opened and closed by application of vacuum or pressure (approx. 60 psi) to the space above the individual valves. Air pressure was used to move the fluids through the channel into the bubble removing chamber.

In an experiment, water containing blue dye (food coloring) was introduced into inlet channel #1 while water containing yellow dye (food coloring) was introduced into inlet channel #2. By opening the appropriate valves and applying 5 psi to the appropriate vent, the following series of fluid movements were carried out: the blue water was moved from inlet channel #1 to the bubble removing chamber; and the yellow water was moved from inlet channel #2 to the bubble removing chamber; a bubble formed between the blue water and the yellow water in the main channel while the yellow water was being introduced. The measured blue water (approximately 1.6 l) was collected into the bubble removing chamber, the yellow water was then collected into the bubble removing chamber where upon the bubble was dispelled and the blue water appeared to form a layer on top of the yellow water. This layered fluid was moved from the bubble removing chamber to a mixing channel and then to a storage chamber.

Functioning of the bubble removing chamber was demonstrated by moving five separate plugs of colored water from the main channel into the bubble removing chamber. The discrete plugs, upon passing into the bubble removing chamber, joined together as a five layered fluid plug.

Example 2

Demonstration of Removing a Bubble within a Liquid

A polycarbonate cartridge was fabricated using conventional machining, forming an array of valves linking a series of channels to a bubble removing chamber which was connected to a venting channel. Elastomeric valves were opened and closed by application of vacuum or pressure (approx. 60 psi) to the space above the individual valves. Air pressure was used to move the fluids back and forth in the channel and through the channel into the bubble removing chamber.

In an experiment, water with an air bubble containing blue dye (food coloring) was introduced into an inlet channel into a main channel. By opening the appropriate valves and applying 5 psi to the appropriate vent, a series of back and forth movement of the blue water in the main channel occurred until the bubble moved to one end of the plug. The blue water with the bubble in front was then collected into the bubble removing chamber where upon the bubble was dispelled.

IV. Conclusion

It is to be understood that the above description is intended to be illustrative and not restrictive. Many variations of the invention will be apparent to those of skill in the art upon reviewing the above description and figures. All cited references, including patent and non-patent literature, are incorporated by reference herein in their entireties for all purposes.

What is claimed is:

1. An apparatus for removing gas bubbles from a mixture of a first fluid and a second fluid, the apparatus comprising:
   a first substrate, wherein the first substrate forms a top surface of a bubble removal chamber;
   a second substrate, wherein the second substrate forms a bottom surface of the bubble removal chamber, wherein the bottom surface comprises a chamber entrance and a substrate coating, wherein a lower portion of the bottom surface comprises a first radius, wherein an upper portion of the bottom surface comprises a second radius, wherein the second radius is different than the first radius, and wherein the substrate coating and the first and second radii are adapted to retain the mixture of the first and second fluids within the lower portion while the gas bubbles dissipate into the chamber;
   a third substrate, wherein the second and third substrates form one or more inlet channels, wherein the one or more inlet channels comprise at least one inlet opening, and wherein the one or more inlet channels are designed to provide fluidic communication between the at least one inlet opening and the bubble removal chamber such that fluids enter the bubble removal chamber through the chamber entrance; and
   a venting channel, wherein the venting channel is connected with the bubble removal chamber and is designed to facilitate the exit of gas from the chamber.

2. The apparatus of claim 1, wherein the substrate coating is hydrophilic.

3. The apparatus of claim 1, wherein the substrate coating is hydrophobic.

4. The apparatus of claim 1, wherein the venting channel is formed by the first and second substrate.

5. The apparatus of claim 1, wherein the first and second radii are in the range of about 1 mm to about 20 mm.

6. A system for removing gas bubbles from a mixture of a first fluid and a second fluid, the system comprising:
   one or more gas bubble removal devices, each device comprising:
      a first substrate, wherein the first substrate forms a top surface of a bubble removal chamber;
      a second substrate, wherein the second substrate forms a bottom surface of the bubble removal chamber, wherein the bottom surface comprises a chamber entrance and a substrate coating, wherein a lower portion of the bottom surface comprises a first radius, wherein an upper portion of the bottom surface comprises a second radius, wherein the second radius is different than the first radius, and wherein the substrate coating and the first and second radii are adapted to retain the mixture of the first and second fluids within the lower portion while the gas bubbles dissipate into the chamber;
      a third substrate, wherein the second and third substrates form one or more inlet channels, wherein the one or more inlet channels comprise at least one inlet opening, and wherein the one or more inlet channels are designed to provide fluidic communication between the at least one inlet opening and the bubble removal chamber such that fluids enter the bubble removal chamber through the chamber entrance;
      a venting channel, wherein the venting channel is connected with the bubble removal chamber and is designed to facilitate the exit of gas from the chamber; and
      an outlet channel, wherein the outlet channel is connected with the bubble removal chamber and is designed to provide fluidic communication between the bubble removal chamber and at least one collection port such that the mixture of the first and second fluids are removed from the chamber through the outlet channel; and
   a source of pressurized gas;
   a plurality of valve mechanisms and a plurality of gates, wherein the valve mechanisms and the plurality of gates are designed to control the input and output of fluids and gas throughout the inlet, venting and outlet channels of the system; and
   a controlling device, wherein the controlling device is designed to manage the input and output of fluids and gas within the system.

7. The system of claim 6, wherein the substrate coating is hydrophilic.

8. The system of claim 6, wherein the substrate coating is hydrophobic.

9. The system of claim 6, wherein the venting channel is formed by the first and second substrate.

10. The system of claim 6, wherein the first and second radii are in the range of about 1 mm to about 20 mm.

11. A method for removing gas bubbles from a mixture of a first fluid and a second fluid, the method comprising:
    providing a gas bubble removal device, the device comprising:
       a first substrate, wherein the first substrate forms a top surface of a bubble removal chamber;
       a second substrate, wherein the second substrate forms a bottom surface of the bubble removal chamber, wherein the bottom surface comprises a chamber entrance and a substrate coating, wherein a lower portion of the bottom surface comprises a first radius, wherein an upper portion of the bottom surface comprises a second radius, wherein the second radius is different than the first radius, and wherein the substrate coating and the first and second radii are adapted to retain the mixture of the first and second fluids within the lower portion while the gas bubbles dissipate into the chamber;
       a third substrate, wherein the second and third substrates form one or more inlet channels, wherein the one or more inlet channels comprise at least one inlet opening, and wherein the one or more inlet channels are designed to provide fluidic communication between the at least one inlet opening and the bubble removal chamber such that fluids enter the bubble removal chamber through the chamber entrance; and
       a venting channel, wherein the venting channel is connected with the bubble removal chamber and is designed to facilitate the exit of gas from the chamber;

introducing a first quantity of the first fluid and a second quantity of the second fluid into the at least one inlet opening; and using pressurized gas to transport the first quantity of the first fluid and the second quantity of the second fluid through the one or more inlet channels and into the bubble removal chamber such that the mixture of the first and second fluids is retained within the lower portion of the bottom surface while the gas bubbles within the mixture are dissipated into the chamber.

12. The method of claim 11, wherein the substrate coating is hydrophilic.

13. The method of claim 11, wherein the substrate coating is hydrophobic.

14. The method of claim 11, wherein the venting channel is formed by the first and second substrate.

15. The method of claim 11, wherein the first and second radii are in the range of about 1 mm to about 20 mm.

* * * * *